(12) United States Patent
Papoutsakis et al.

(10) Patent No.: US 12,338,431 B2
(45) Date of Patent: Jun. 24, 2025

(54) SYNTROPHIC CO-CULTURES AND USES THEREOF

(71) Applicants: Eleftherios T. Papoutsakis, Newark, DE (US); Kamil Charubin, Newark, DE (US); Alexander A. Mitkas, Newark, DE (US)

(72) Inventors: Eleftherios T. Papoutsakis, Newark, DE (US); Kamil Charubin, Newark, DE (US); Alexander A. Mitkas, Newark, DE (US)

(73) Assignee: University of Delaware, Newark, DE (US)

( * ) Notice: Subject to any disclaimer, the term of this patent is extended or adjusted under 35 U.S.C. 154(b) by 45 days.

(21) Appl. No.: 16/327,695

(22) PCT Filed: Aug. 23, 2017

(86) PCT No.: PCT/US2017/048176
§ 371 (c)(1),
(2) Date: Feb. 22, 2019

(87) PCT Pub. No.: WO2018/039319
PCT Pub. Date: Mar. 1, 2018

(65) Prior Publication Data
US 2019/0218505 A1 Jul. 18, 2019

Related U.S. Application Data

(60) Provisional application No. 62/378,339, filed on Aug. 23, 2016, provisional application No. 62/526,586, filed on Jun. 29, 2017.

(51) Int. Cl.
C12N 1/20 (2006.01)
C12P 1/04 (2006.01)
(Continued)

(52) U.S. Cl.
CPC .......... *C12N 1/20* (2013.01); *C12P 1/04* (2013.01); *C12P 7/04* (2013.01); *C12P 7/065* (2013.01);
(Continued)

(58) Field of Classification Search
CPC ...... C12N 1/20; C12P 1/04; C12P 7/14; C12P 7/04; C12P 7/065; C12P 7/10; C12P 7/16;
(Continued)

(56) References Cited

U.S. PATENT DOCUMENTS

2009/0001781 A1  1/2009  Karube et al.
2009/0203100 A1  8/2009  Simpson et al.
(Continued)

OTHER PUBLICATIONS

Pattra et al., Bio-hydrogen production from the fermentation of sugarcane bagasse hydrolysate by Clostridium butyricum, International Journal of Hydrogen Energy, vol. 33, (2008), pp. 5256-5265.*
(Continued)

*Primary Examiner* — Jennifer M. H. Tichy
(74) *Attorney, Agent, or Firm* — Buchanan Ingersoll & Rooney PC

(57) ABSTRACT

Syntrophic co-cultures containing at least two microorganisms, wherein (a) at least one of the microorganisms is a solventogen able to metabolize biomass to produce metabolic byproduct(s) therefrom, (b) at least one of the microorganisms is a microorganism different from the solventogen, wherein the microorganism different from the primary solventogen depends on the metabolites and/or the metabolism of the primary solventogen for survival and growth and is able to fix or metabolize the metabolic byproducts produced by the solventogen to produce metabolic byproduct(s) therefrom, and (c) the solventogen is able to metabolize the metabolic byproduct(s) produced by the microorganism different from the solventogen to produce further metabolic byproducts, such as liquid fuels and commodity chemicals,
(Continued)

as well as methods for using these syntrophic co-cultures to produce such products via fermentation, are disclosed.

16 Claims, 19 Drawing Sheets

(51) Int. Cl.
| | |
|---|---|
| *C12P 7/04* | (2006.01) |
| *C12P 7/06* | (2006.01) |
| *C12P 7/10* | (2006.01) |
| *C12P 7/14* | (2006.01) |
| *C12P 7/16* | (2006.01) |
| *C12P 7/28* | (2006.01) |
| *C12P 7/40* | (2006.01) |
| *C12P 39/00* | (2006.01) |

(52) U.S. Cl.
CPC .............. *C12P 7/10* (2013.01); *C12P 7/14* (2013.01); *C12P 7/16* (2013.01); *C12P 7/28* (2013.01); *C12P 7/40* (2013.01); *C12P 39/00* (2013.01); *C12P 2203/00* (2013.01); *Y02E 50/10* (2013.01)

(58) Field of Classification Search
CPC .... C12P 7/28; C12P 7/40; C12P 39/00; C12P 2203/00; Y02E 50/10
USPC ......................................................... 435/373
See application file for complete search history.

(56) References Cited

U.S. PATENT DOCUMENTS

| | | | |
|---|---|---|---|
| 2010/0143985 A1 | 6/2010 | Lee et al. | |
| 2011/0059499 A1* | 3/2011 | Simpson ............... | C12P 7/16 435/155 |
| 2012/0107888 A1* | 5/2012 | Schmalisch ............ | C12P 7/10 435/155 |
| 2014/0206066 A1 | 7/2014 | Datta et al. | |
| 2014/0220648 A1* | 8/2014 | Barr ....................... | C12N 15/52 435/156 |
| 2014/0273121 A1 | 9/2014 | Datta et al. | |
| 2015/0176035 A1 | 6/2015 | Green et al. | |
| 2016/0068919 A1 | 3/2016 | Chen et al. | |
| 2016/0215302 A1* | 7/2016 | Haas ....................... | C12P 7/14 |
| 2016/0281115 A1 | 9/2016 | Hickey | |
| 2016/0298143 A1 | 10/2016 | Reeves et al. | |

OTHER PUBLICATIONS

Namour, The biogeochemical origin of sewage gases and control of their generation, Journal of Hazardous Materials Advances, 7 (2022), pp. 1-18.*

International Preliminary Report on Patentability for International Application No. PCT/US2017/048176, dated Feb. 26, 2019—5 pages.
International Search Report and Written Opinion for International Application No. PCT/US2017/048176, dated Nov. 14, 2017—7 pages.
Fast et al., Acetogenic Mixotrophy: Novel Options for Yield Improvement in Biofuels and Biochemicals Production, Current Opinion in Biotechnology, 33:60-72 (2015).
Lubitz et al., "Hydrogenases", Chemical Reviews, 114:4081-4148 (2014).
Meyer et al., "The Effect of CO on Growth and Product Formation in Batch Cultures of Clostridium Acetobutylicum", Biotechnology Letters, 7(1):37-42 (1985).
Purec et al., "The Inhibition of Hydrogenase by Carbon Monoxide and the Reversal of This Inhibition by Light", Biochemistry, 1(2):270-275 (1962).
Tomlinson et al., "Carbon Dioxide and Acetate Utilization by Clostridium Kluyveri", Journal of Biological Chemistry, 209:585-595 (1954).
Dubey et al., "Intercellular Nanotubes Mediate Bacterial Communication", Cell, 144:590-600 (2011).
Pande et al., "Metabolic Cross-Feeding via Intercellular Nanotubes Among Bacteria", Nature Communications, 2015, 6:6238, DOI:10.1039/ncomms7238, 13 pages.
Dubey et al., "Architecture and Characteristics of Bacterial Nanotubes", Developmental Cell, 36:453-461 (2016).
Kato et al., "Microbial Interspecies Electron Transfer via Electric Currents Through Conductive Minerals", PNAS, 109(25):10042-10046 (2012).
Almstrand et al., "New Methods for Analysis of Spatial Distribution and Coaggregation of Microbial Populations in Complex Biofilms", Applied and Environmental Microbiology, 79(19):5978-5987 (2013).
Salimi et al., "Characterizing Metabolic Interactions in a Clostridial Co-Culture for Consolidated Bioprocessing", BMC Biotechnology, 13:95, 9 pages (2013).
Kim et al., "Control of Carbon and Electron Flow in Clostridium Acetobutylicum Fermentations: Utilization of Carbon Monoxide to Inhibit Hydrogen Production and to Enhance Butanol Yields", Applied and Environmental Microbiology, 48(4);764-770 (1984).
Kiyoshi et al., "Butanol Production from Alkali-Pretreated Rice Straw by Co-Culture of CLostridium Thermocellum and Clostridium Saccharoperbutylacetonicum", Bioresource Technology, 186:325-328 (2015).
Xu et al., "Immobilized Anaerobic Fermentation for Bio-Fuel Production by Clostridium Co-Culture", Bioprocess Biosyst Eng., 37:1551-1559 (2014).
Diender et al., "Production of Medium-Chain Fatty Acids and Higher Alcohols by a Synthetic Co-Culture Grown on Carbon Monoxide or Syngas", Biotechnology for Biofuels, 9:82, 11 pages (2016).
Rabemanolontsoa et al., "High Conversion Efficiency of Japanese Cedar Hydrolyzates Into Acetic Acid by Co-Culture of Clostridium Thermoceticum and Clostridium Thermocellum", J. Chem Technol Biotechnol, 91:1040-1047 (2016).

* cited by examiner

SYNTROPHIC CO-CULTURES AND USES THEREOF

CROSS-REFERENCE TO RELATED APPLICATIONS

This application is the national phase of International Application No. PCT/US2017/048176, filed Aug. 23, 2017, which claims priority to U.S. Provisional Patent Application Ser. No. 62/378,339, filed Aug. 23, 2016, and U.S. Provisional Patent Application Ser. No. 62/526,586, filed Jun. 29, 2017, the disclosures of each of which are hereby incorporated by reference herein in their entirety.

STATEMENT REGARDING FEDERALLY SPONSORED RESEARCH OR DEVELOPMENT

This invention was made with government support under Grant No. CBET-1511660, awarded by the U.S. National Science Foundation (NSF), and Grant No. 1144726, awarded by the Integrative Graduate Education and Research Traineeship (IGERT) fellowship sponsored by the NSF. The government has certain rights in the invention.

FIELD OF THE INVENTION

The present disclosure is generally directed to syntrophic co-cultures comprising at least two microorganisms, wherein (a) at least one of the microorganisms is a solventogen able to metabolize biomass to produce metabolic byproduct(s) therefrom, (b) at least one of the microorganisms is a microorganism different from the solventogen, wherein the microorganism different from the primary solventogen depends on the metabolites and/or the metabolism of the primary solventogen for survival and growth and is able to fix or metabolize the metabolic byproducts produced by the solventogen to produce metabolic byproduct(s) therefrom, and (c) the solventogen is able to metabolize the metabolic byproduct(s) produced by the microorganism different from the solventogen to produce further metabolic byproducts, such as liquid fuels and commodity chemicals, as well as to methods for using these syntrophic co-cultures to produce such products via fermentation.

BACKGROUND OF THE INVENTION

Currently, fossil fuels such as methane, coal, and crude oil are used to generate electricity and heat, as well as to power our vehicles. In the process, large amounts of $CO_2$ are released into the environment. As a result, in 2014 alone a total of 36 gigatonnes of $CO_2$ were emitted globally. This is problematic, since $CO_2$ is a greenhouse gas and its release into the environment leads to increasing global temperatures and climate change. Further $CO_2$ emissions can be reduced in two ways. First, conventional fuels derived from fossil fuels can be replaced with biofuels which have a lower carbon footprint. Second, $CO_2$ waste can be used as feedstock to produce biofuels, such as ethanol and n-butanol, and other commodity chemicals such as, acetone, acetoin, and 2,3-butanediol.

Biofuels are fuels that are derived from organic materials, such as plant biomass and animal waste. Plant biomass encompasses conventional food plants, specialty energy crops, such as switchgrass, as well as plant waste, such as corn stover and wheat straw. Biomass is composed of three major components which are cellulose (37 to 38%), hemicellulose (26 to 28%), and lignin (14 to 20%). The remaining balance consists of various proteins and ash.

Biomass can be converted into biofuels and other chemicals through biological or chemical means. Chemical conversion of biomass to biofuels consists of a gasification process where biomass is converted to syngas (i.e., a mixture of $H_2$, CO, and $CO_2$), which then can be converted to liquid fuels through the Fischer-Tropsch process. Currently, the Fischer-Tropsch process is not economically feasible due to high capital costs and low conversion efficiencies. Therefore, bioconversion is a promising alternative because of its high specificity and process efficiencies under mild operation conditions.

Unfortunately, it is difficult to find or engineer a single organism that can fully utilize all components of biomass and convert them to biofuels and/or commodity chemicals. Furthermore, conventional fermentation processes lose at the least one third of all carbon stored in the sugar substrate during the breakdown of sugar molecules. Thus, there exists a continuing need for improved bioconversion systems capable of more efficiently converting biomass to biofuels and/or commodity chemicals.

BRIEF SUMMARY OF THE INVENTION

This need is met by the syntrophic co-cultures and the methods of using such syntrophic co-cultures for producing a fermentation product according to the present invention.

Thus, one embodiments of the present invention is a syntrophic co-culture comprising at least two microorganisms, wherein (a) at least one of the at least two microorganisms is a primary solventogen able to metabolize at least one biomass component to produce at least one metabolic byproduct therefrom, (b) at least one of the at least two microorganisms is a microorganism different from the primary solventogen, wherein the microorganism different from the primary solventogen depends on the metabolites and/or the metabolism of the primary solventogen for survival and growth and is able to fix or metabolize the at least one metabolic byproduct produced by the primary solventogen to produce at least one metabolic byproduct therefrom, and (c) the primary solventogen is able to metabolize the at least one metabolic byproduct produced by the microorganism different from the primary solventogen to produce at least one further metabolic byproduct.

Another embodiment of the present invention is a method for producing a fermentation product comprising (a) providing the above syntrophic co-culture, (b) combining the syntrophic co-culture with at least one biomass component to form a mixture, and (c) fermenting the mixture to provide at least one fermentation product. In certain embodiments, the method further comprises the addition of $CO_2$, CO, $H_2$, and mixtures thereof during fermentation of the mixture.

In certain embodiments, the primary solventogen Is a microorganism selected from the group consisting of solventogenic microorganisms of the genus *Clostridium*. In certain of embodiments, the primary solventogen is a microorganism selected from the group consisting of *Clostridium acetobutylicum, Clostridium beijerinckii, Clostridium tyrobutyricum, Clostridium pasteurianum, Clostridium saccharobutylicum, Clostridium saccharoperbutylacetonicum, Clostridium butyricum, Clostridium cellulovorans*, and solventogenic Clostridia from the NRRL, DSMZ, NCIMB, and JCM culture collections.

In certain embodiments, the at least one biomass component is selected from the group consisting of $C_5$ and $C_6$ sugars, oligosaccharides, hemicellulose, cellulose, starches, and carbohydrate-rich renewable substrates.

In certain embodiments, the syntrophic co-culture comprises at least two microorganisms different from the primary solventogen.

In certain embodiments, the microorganism different from the primary solventogen is selected from the group consisting of acetogenic microorganisms of the class Clostridia and genus *Clostridium*. In certain embodiments, the microorganism different from the primary solventogen is an acetogenic microorganism selected from the group consisting of *Clostridium carboxidivorans*, *Clostridium autoethanogenum*, *Clostridium ljungdahlii*, *Acetobacterium woodii*, *Moorella thermoacetica*, and *Eubacterium limosum*. In certain embodiments, the microorganism different from the primary solventogen is *Clostridium kluyveri*.

In certain embodiments, the at least one further metabolic byproduct produced is selected from the group consisting of linear and branched $C_2$ to $C_9$ alcohols, diols, aldehydes, ketones, carboxylic acids, and mixtures thereof. In certain embodiments, the at least one further metabolic byproduct produced is selected from the group consisting of ethanol, propanols, butanols, pentanols, hexanols, octanols, acetone, butyric acid, acetic acid, caproic acid, butanediols, acetoin, hydroxyl acids, and mixtures thereof. In certain embodiments, the at least one further metabolic byproduct produced is selected from the group consisting of acetoin, acetone, ethanol, isopropanol, n-butanol, 2,3-butanediol, n-hexanol, n-octanol, and mixtures thereof.

In certain embodiments, the primary solventogen and/or microorganism different from the primary solventogen are selected from the group consisting of facultative anaerobes, microorganisms of the genus *Bacillus*, microorganisms of the genus *Lactobacillus*, and microorganisms of the genus *Lactococcus*. In certain embodiments, the primary solventogen and/or the microorganism different from the primary solventogen is *Escherichia coli*.

In certain embodiments, the syntrophic co-culture comprises *Clostridium acetobutylicum* and *Clostridium ljungdahlii*. In certain embodiments, the syntrophic co-culture comprises *Clostridium acetobutylicum* and *Clostridium kluyveri*. In certain embodiments, the syntrophic co-culture comprises *Clostridium acetobutylicum*, *Clostridium ljungdahlii*, and *Clostridium kluyveri*. In certain embodiments, the syntrophic co-culture comprises an acetone-producing strain of *Escherichia coil* (EcoA) and *Clostridium ljungdahlii*.

In certain embodiments, the primary solventogen and the microorganism different from the primary solventogen are present in the syntrophic co-culture in a ratio in the range of from 1:1 to 1:20.

In certain embodiments, the at least one metabolic byproduct produced by the primary solventogen comprises $CO_2$ and $H_2$. In certain embodiments, the at least one metabolic byproduct produced by the primary solventogen further comprises acetate and ethanol. In certain embodiments, the at least one metabolic byproduct produced by the primary solventogen further comprises acetoin and acetone. In certain embodiments, the at least one metabolic byproduct produced by the microorganism different from the primary solventogen is selected from the group consisting of acetate, butyrate, hexanoate, octanoate, and ethanol.

DETAILED DESCRIPTION OF THE INVENTION

Figure 1:
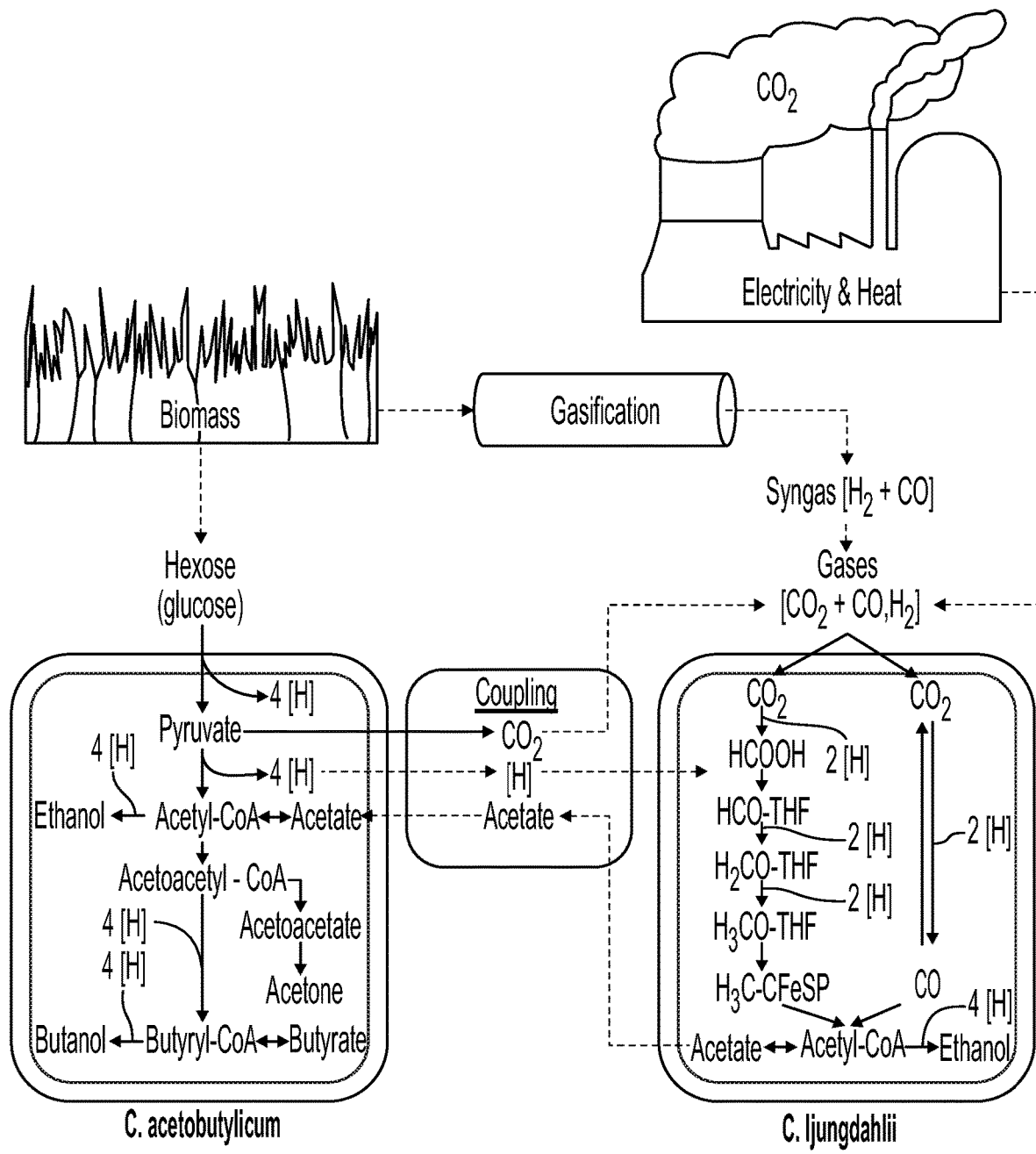
FIG. 1 schematically depicts an overview of the major metabolic pathways found in a co-culture of *C. acetobutylicum* and *C. ljungdahlii*, the predicted metabolic coupling between both organisms, and a summary of the net yield of electrons and hydrogen ions from the major reactions in each organism.

The following will describe some embodiments of the present invention in detail. However, without departing from the spirit of the present invention, the present invention may be embodied in various embodiments and should not be limited to the embodiments described in the specification. In addition, unless otherwise indicated herein, the expressions "a," "an", "the", or the like recited herein are intended to include the singular and plural forms.

In one aspect of the present invention, the present disclosure provides for a stable, robust syntrophic co-culture comprising at least two microorganisms, wherein (a) at least one of the at least two microorganisms is a primary solventogen able to metabolize at least one biomass component to produce at least one metabolic byproduct therefrom, (b) at least one of the at least two microorganisms is a microorganism different from the primary solventogen, wherein the microorganism different from the primary solventogen depends on the metabolites and/or the metabolism of the primary solventogen for survival and growth and is able to fix or metabolize the at least one metabolic byproduct produced by the primary solventogen to produce at least one metabolic byproduct therefrom, and (c) the primary solventogen is able to metabolize the at least one metabolic byproduct produced by the microorganism different from the primary solventogen to produce at least one further metabolic byproduct. The at least two microorganisms of the syntrophic co-culture according to the present invention engage in processes that includes beneficial exchange of electrons and metabolites that enhance the stability of the syntrophic co-culture, maximize the production of desirable metabolites, and minimize the production of $CO_2$ and undesirable byproducts. The at least two microorganisms of the syntrophic co-culture according to the present invention also engage in processes that includes membrane fusion in order to maximize the effectiveness of electron and metabolite exchange to benefit the microorganisms and the fermentation-process outcomes in terms of metabolite yields and selectivity.

The syntrophic co-cultures according to the present invention offer three advantages over conventional fermentation. First, in certain embodiments where at least one of the microorganisms different from the primary solventogen is an acetogen, $CO_2$ fixation by the acetogen(s) will improve the carbon balance of the process by assimilating all of carbon present in the sugar substrate. Second, in certain embodiments where the syntrophic co-culture contains both solventogenic and acetogenic organisms, the co-culture will be able to consume a mixed feed of a sugar substrate and inorganic $CO_2$, $H_2$, and CO gasses. Finally, the syntrophic co-cultures according to the present invention will produce higher solvent titers due to complete assimilation of carbon contained in the biomass-derived substrate. The strains of the at least two microorganisms of the syntrophic co-culture can be naturally occurring, genetically engineered to express certain traits, or any combination thereof.

As used herein, the term "syntrophic co-culture" refers to a culture containing at least two microorganisms, wherein the at least two microorganisms exist in a syntrophic relationship, i.e., one or more of the at least microorganism depends on nutrients and/or substrates produced by another microorganism in the co-culture for its growth and/or survival. In embodiments according to the present invention, the primary solventogen and the microorganism different from the primary solventogen exist in a syntrophic relationship with each other, whereby the primary solventogen uses all or some components of the biomass as substrate, while the microorganism different from the primary solventogen depends for growth and/or survival on the byproducts produced by the metabolism of the biomass substrate by the primary solventogen, while the byproducts of the metabolism of the microorganism different from the primary solventogen are utilized and/or benefit the metabolism and growth of the primary solventogen.

As used herein, the term "solventogen" refers to anaerobic or microaerobic microorganisms that can metabolize sugars and/or more complex biomass substrates to metabolically produce various metabolites, including small organic molecules such as alcohols, carboxylic acids, and ketones, capable of use as liquid biofuels and other desirable organic commodity chemicals. As used herein, the term "primary solventogen" refers to anaerobic or microaerobic microorganisms that can metabolize sugars and/or more complex biomass substrates to metabolically produce various metabolites, including small organic molecules such as alcohols, carboxylic acids, and ketones, capable of use as liquid biofuels and other desirable organic commodity chemicals and that, when used in the syntrophic co-cultures according to present invention, produces at least one metabolic byproduct from the metabolism of at least one biomass component, which can be fixed or metabolized by the microorganism(s) different from the primary solventogen and metabolizes at least one metabolic byproduct produced by the microorganism(s) different from the primary solventogen to produce a further metabolic byproduct, such as liquid biofuels and other desirable organic commodity chemicals.

As used herein, the term "acetogen" refers to anaerobic microorganisms that utilize a version of the Wood-Ljungdahl (WL) pathway to employ $CO_2$ and $H_2$ and/or CO for autotrophic growth, and which produce acetate and ethanol as their main metabolites, but also small amounts of more complex metabolites when grown on $CO_2$ and $H_2$ and/or CO alone. In certain instances, these microorganisms can also metabolize more complex $C_1$ molecules, such as methanol and formate, and also some more complex organic molecules. When grown alone on more complex organic molecules as substrates, acetogens can produce more complex metabolites.

The syntrophic co-culture according to the present invention can employ one or more suitable solventogenic microorganisms as the primary solventogen. In certain embodiments, the primary solventogen is a microorganism selected from the group consisting of solventogenic microorganisms of the genus *Clostridium*. Bacteria of the genus *Clostridium* belong to the phylum Firmicute. Clostridia are anaerobic, Gram-positive, rod-shaped bacteria. They play important roles in the human and animal health, anaerobic degradation of simple and complex sugars, including cellulosic biomass, acetogenesis, and the carbon-cycle on earth, as well as bioremediation of complex organic chemicals. Due to their various functions, clostridia can be grouped into multiple groups depending on their metabolic capabilities. As such, solventogenic clostridia such as *Clostridium acetobutylicum* (hereinafter referred to as "Cac"), *Clostridium beijerinckii*, and *Clostridium butyricum* are capable of consuming various sugar substrates to produce carboxylic acids (e.g., acetic and butyric acids) and solvents (e.g., butanol, ethanol, and acetone). Specifically, Cac can produce commodity chemicals like acetone, butanol, ethanol, and acetoin in a process known as the ABE fermentation. In the process, Cac releases $H_2$ and $CO_2$ gases as waste. On the other hand, cellulolytic clostridia such as *Clostridium thermocellum* and *Clostridium cellulolyticum*, as the names suggest, are capable of breaking down cellulose, which is one of the major components of plant biomass. Finally, acetogenic clostridia, such as *Clostridium ljungdahlii* (hereinafter referred to as "Clj"), *Clostridium thermoaceticum*, and *Clostridium carboxidivorans* are capable of consuming $CO_2$ gas through the Wood-Ljungdahl (WL) pathway. Thus, a syntrophic co-culture system comprising clostridia organisms from each of these groups would be capable of consuming a diverse, mixed feed of sugar and inorganic gas substrates.

Examples of solventogenic clostridia that can be used as the primary solventogen according to the present invention include, but are not limited to, *Clostridium acetobutylicum*, *Clostridium beijerinckii*, *Clostridium butylicum*, *Clostridium tyrobutyricum*, *Clostridium pasteurianum*, *Clostridium saccharobutylicum*, *Clostridium saccharoperbutylacetonicum*, *Clostridium akagii*, *Clostridium algidicarnis*, *Clostridium arbusti*, *Clostridium argentinense*, *Clostridium aurantibutylicum*, *Clostridium Clostridium neopropionicum*, *Clostridium ragsdalei*, *Clostridium saccharoacetobutylicum*, *Clostridium sporogenes*, *Clostridium tetanomorphum*, *Clostridium thermoaceticum*, *Clostridium thermocellum*, *Clostridium aurantibutyricum*, *Clostridium thermobutyricum*, *Clostridium butyricum*, *Clostridium cellulovorans*, and the solventogenic Clostridia from the NRRL, DSMZ, NCIMB, and JCM culture collections.

In certain embodiments, the primary solventogen can be a microorganism other than a solventogenic *Clostridium*. Such microorganisms include facultative and obligate anaerobes or aerobes that can form stable syntrophic cultures with acetogens. Such microorganisms include genetically modified *Escherichia coli* and various native or engineered *Bacillus*, *Lactocabacillus*, or *Lactococcus* microorganisms engineered to produce a large spectrum of metabolites as industrial chemicals or fuels. In certain embodiments, such microorganisms include recombinant *Escherichia coli* strains that can produce metabolites such as acetone, butanols, butanediols, and more complex organic molecules. Other examples include Clostridia that do not produce significant amounts of solvents, such as alcohols or ketones, but rather produce only carboxylic acids. Further examples include combining archaea microorganisms capable of growing anaerobically on methane or other microorganisms that produce molecules such as methanol or acetate with acetogens and other clostridia that would utilize the methanol and/or acetate together with sugars. For purposes of the present invention, these microorganisms are considered to be solventogens, as defined herein.

The primary solventogens according to the present invention can metabolize any suitable component of biomass so as to produce at least one metabolic byproduct capable of being fixed or metabolized by the microorganism different from the primary solventogen. Examples of such biomass components include, but are not limited to, $C_5$ and $C_6$ monosaccharides, oligosaccharides, complex polysaccharides like molasses, starch, cellulose, and hemicellulose, as well as other carbohydrate-rich renewable substrates. Specific examples of biomass components include, but are not limited to monosaccharides (e.g., glucose, fructose, galactose, mannose, arabinose, lyxose, ribose, xylose, ribulose, xylulose, allose, altrose, gulose, idose, talose, psicose, sorbose, tagatose); disaccharides (e.g., sucrose, maltose, lactose, lactulose, trehalose, cellobiose); oligosaccharides (e.g., stachyose, maltotriose, maltotetrose, maltopentaose); and polysaccharides (e.g., starch, cellulose, glycogen, cyclodextrin, arabinoxylans, guar gum, gum arabic, chitin, gum, alginate, pectin, gellan). The composition of the biomass component used as substrate can be designed in order to maximize the effectiveness of electron and metabolite exchange to benefit the microorganisms and the fermentation-process outcomes in terms of metabolite yields and selectivity.

The primary solventogen according to the present invention can produce any metabolic byproduct from metabolism of the biomass component suitable for fixing or metabolization by the microorganism different from the primary solventogen. Examples of such metabolic byproducts include, but are not limited to, CO, $CO_2$, $H_2$, acetate, ethanol, acetoin, and acetone.

The microorganism different from the primary solventogen according to the present invention can be any suitable microorganism that depends on the metabolites and/or the metabolism of the primary solventogen for survival and growth and is capable of fixing or metabolizing the metabolic byproduct(s) produced by the primary solventogen so as to produce metabolic byproduct(s) capable of being metabolized by the primary solventogen. In certain embodiments, the microorganism different from the primary solventogen can be an acetogenic microorganism and/or another solventogenic microorganism. In certain embodiments, the microorganism different from the primary solventogen can be a microorganism such as *Clostridium kluyveri*. *Clostridium kluyveri* is not an acetogen, such as *Clostridium ljungdahlii*. But, like the acetogens, it is useful in the syntrophic co-cultures according to the present invention, since it depends on the primary solventogen for survival by providing it with ethanol and acetate or butyrate, which the *Clostridium kluyveri* can metabolize to produce hexanoate.

In certain embodiments, the microorganism different from the primary solventogen is selected from the group consisting of acetogenic microorganisms of the class Clostridia and genus *Clostridium*, as disclosed above. Examples of such acetogenic microorganisms include, but are not limited to, *Acetitomaculum ruminis*, *Acetoanaerobium noterae*, *Acetoanaerobium romashkovii*, *Acetobacterium bakii*,

*Acetobacterium carbinolicum, Acetobacterium dehalogenans, Acetobacterium fimetarium, Acetobacterium malicum, Acetobacterium paludosum, Acetobacterium psammolithicum, Acetobacterium tundra, Acetobacterium wieringae, Acetobacterium woodii, Acetobacterium* sp. AmMan1, *Acetobacterium* sp. B10, *Acetobacterium* sp. HA1, *Acetobacterium* sp. HP4, *Acetobacterium* sp. KoB58, *Acetobacterium* sp. LuPhet1, *Acetobacterium* sp. LuTria3, *Acetobacterium* sp. MrTac1, *Acetobacterium* sp. OyTac1, *Acetobacterium* sp, RMMac1, *Acetobacterium* sp. 69, *Acetohalobium arabaticum, Acetonema longum, Bryantella formatexigens, Butyribacterium methylotrophicum, Caloramator fervidus, Clostridium aceticum, Clostridium autoethanogenum, Clostridium carboxidivorans, Clostridium coccoides, Clostridium difficile* AA1, *Clostridium drakei, Clostridium formicaceticum, Clostridium glycolicum* 22, *Clostridium glycolicum* RD-1, *Clostridium ljungdahlii, Clostridium magnum, Clostridium mayombei, Clostridium methoxybenzovorans, Clostridium scatologenes, Clostridium ultunense, Clostridium* sp. CV-AA1, *Clostridium* sp. M5a3, *Clostridium* sp. F5a15, *Clostridium* sp. Ag4f2, *Clostridium* sp. TLN2, *Eubacterium aggregans, Eubacterium limosum, Holophaga foetida, Moorella glycerini, Moorella mulderi, Moorella thermoacetica, Moorella thermoautotrophica, Moorella* sp. F21, *Moorella* sp. HUC22-1, *Natroniella acetigena, Natronincola histidinovorans, Oxobacter pfennigii, Ruminococcus hydrogenotrophicus, Ruminococcus productus, Ruminococcus productus, Ruminococcus schinkii, Ruminococcus* sp. TLF1, *Sporomusa acidovorans, Sporomusa aerivorans, Sporomusa malonica, Sporomusa ovate, Sporomusa paucivorans, Sporomusa silvacetica, Sporomusa sphaeroides, Sporomusa termitida, Sporomusa* sp. DR6, *Sporomusa* sp. DR1/8, *Syntrophococcus sucromutans, Thermoacetogenium phaeum, Thermoanaerobacter kivui, Tindallia califomiensis, Treponema azotonutricium*, and *Treponema primitia*.

The microorganism different from the primary solventogen according to the present invention can produce any metabolic byproduct from metabolism of the metabolic byproduct produced by the primary solventogen suitable for metabolization by the primary solventogen. Examples of such metabolic byproducts include, but are not limited to, acetate, butyrate, hexanoate, octanoate, and ethanol.

The primary solventogen according to the present invention can metabolize the metabolic byproduct(s) produced by the microorganism different from the primary solventogen to produce at least one further metabolic byproduct. These further metabolic byproducts can be organic molecules useful as solvents, biofuels, and commodity chemicals. General classes of such organic molecules include, but are not limited to, linear and branched $C_2$ to $C_9$ alcohols, diols, aldehydes, ketones, and carboxylic acids. More specific examples include, but are not limited to, ethanol, propanols, butanols, pentanols, hexanols, octanols, acetone, butyric acid, acetic acid, caproic acid, butanediols, acetoin, and hydroxyl acids. Even more specific examples include, but are not limited to, acetoin, acetone, ethanol, isopropanol, n-butanol, 2,3-butanediol, n-hexanol, n-octanol.

In certain embodiments, the final further metabolic byproduct mixture only includes alcohols, such as isopropanol, 2,3-butanediol, butanol, hexanol, and octanol (i.e., all acid and ketone intermediates are converted to alcohol products). The relative amounts of each alcohol can be controlled through growth conditions and genetic manipulation of each organism in the consortium. For example, in certain embodiments 2,3-butanediol titer can be increased by feeding the system exogenous $H_2$ gas in order to stimulate acetoin production by *Clostridium acetobutylicum*. In certain other embodiments, isopropanol titer can be increased by using a recombinant *Clostridium acetobutylicum* where acetone producing genes were overexpressed. In certain other embodiments, acetone production can be recovered by using a recombinant *Clostridium ljungdahlii* whose SADH gene has been deleted or inactivated. In certain other embodiments, the fermentation pH can be maintained at a specific level in order to modulate the relative amounts of produced hexanol and octanol.

In certain embodiments, the syntrophic co-cultures according to the present invention can comprise two or more primary solventogens and/or two or more two microorganisms different from the primary solventogen, so as to construct synthetic, stable co-cultures that benefit the fermentation-process outcomes in terms of metabolite yields and selectivity, and substrate utilization. In certain embodiments, any number and combination of the solventogens and acetogens listed above can be combined to engineer stable, syntrophic co-cultures according to the present invention, such as stable, syntrophic co-cultures comprising three or more microorganisms.

Figure 2:
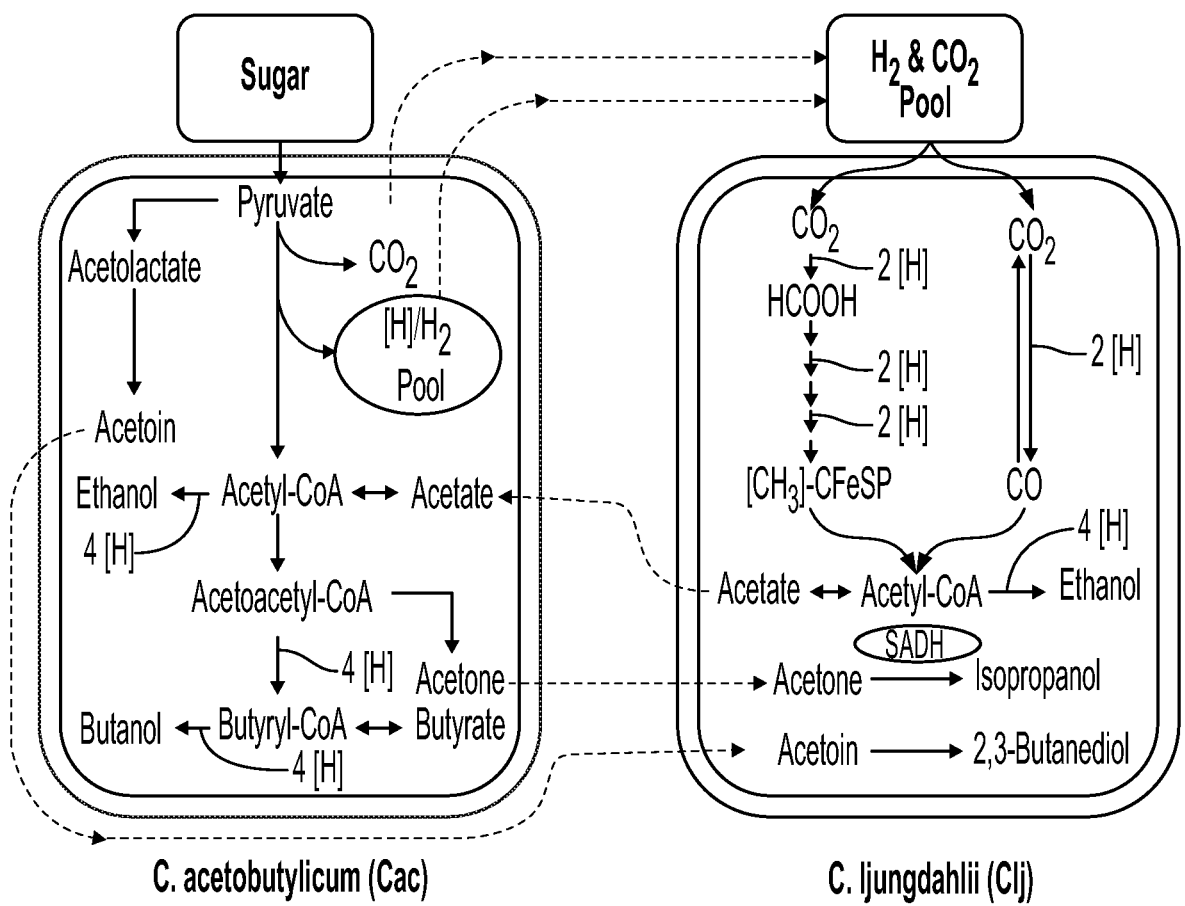
FIG. 2 schematically depicts an overview of the major metabolic pathways found in a co-culture of *C. acetobutylicum* and *C. ljungdahlii*, the predicted metabolic coupling between both organisms, and a summary of the net yield of electrons and hydrogen ions from the major reactions in each organism.

In one particular embodiment, the syntrophic co-culture according to the present invention comprises a combination of primary solventogen *Clostridium acetobutylicum* (Cac) and acetogen *Clostridium ljungdahlii* (Clj). As shown in FIGS. 1 and 2, Clj is co-cultured together with Cac. In this system, the main feedstock is sugar. Cac is able to utilize a wide variety of monosaccharides (e.g., glucose, fructose, xylose, etc.) and polysaccharide sources (e.g., starch, hemicellulose, molasses, etc.). In comparison to Cac, Clj is limited in its ability to consume a broad spectrum of sugars. Notably Clj is unable to consume glucose. Furthermore, Clj grows at much slower rates, and at low cell densities. In the process Cac produces acetone, ethanol, and butanol in a process known as the ABE fermentation. During the fermentation, Cac releases approximately one third of the sugar substrate as $CO_2$ waste and converts any excess reducing equivalents into $H_2$ gas. In comparison, Clj is able to consume $CO_2$ in the presence of an electron source, such as $H_2$ or CO gasses, through the Wood-Ljungdahl (hereinafter, "WL") pathway to produce acetate and ethanol. In the co-culture, Clj consumes waste $CO_2$ and $H_2$ (or reducing equivalents) released by Cac to produce additional acetate and ethanol. Next, Cac reabsorbs the additional acetate produced by Clj to produce more butanol and acetone. As a result, the Cac/Clj co-culture is able to convert a higher fraction of the sugar substrate into usable products by fixing gaseous waste released by Cac. Furthermore, the Cac/Clj co-culture was also found to produce relatively large amounts of isopropanol (2-propanol) and 2,3-butanediol. In the case of isopropanol, neither microorganism is able to produce it on its own. In the co-culture, Clj is able to reduce acetone produced by Cac into isopropanol due to actions of a promiscuous secondary alcohol dehydrogenase (SADH). In the case of 2,3-butanediol, Clj was found to produce small amounts (1 to 2 mM) using its native pathways. In comparison, the Cac/Clj co-culture is able to produce 20 to 30 mM of 2,3-butanediol, where Clj reduces acetoin produced by Cac.

As shown in FIGS. 1 and 2, Cac and Clj will couple their metabolic pathways when grown together in a co-culture. Cac can break down hexose sugars (e.g., glucose) through the glycolysis pathway to produce 2 molecules of acetyl-CoA and 2 molecules of $CO_2$ per one molecule of sugar. In the process, Cac generates a net amount of 8 electrons, and 2 ATP molecules per glucose molecule. Next, the pool of reducing equivalents, i.e., electrons, can be used to reduce acetyl-CoA to solvents, such as ethanol and butanol. The conversion of acetyl-CoA to ethanol requires 4 electrons, while production of butanol involves the condensation of two acetyl-CoA molecules and a total of 8 electrons. In comparison, Clj can condense 2 molecules of $CO_2$ into one molecule of acetyl-CoA through the WL pathway. The WL pathway consists of two branches called the methyl and carbonyl branch. In the carbonyl branch, one molecule of $CO_2$ is converted to CO, which requires an input of 2 electrons. In the methyl branch, the second $CO_2$ molecule is converted to 5-methyltetrahydrofolate in a stepwise fashion, which requires a total of 6 electrons and one ATP molecule. Finally, CO and 5-methyltetrahydrofolate are condensed together with the CoA group to produce acetyl-CoA. When compared to Cac, Clj is limited in its solventogenic capabilities and, as a result, can only convert acetyl-CoA to acetate and ethanol. In summary, glycolysis in Cac and the WL pathway in Clj are compatible in that the 2 molecules of $CO_2$ and 8 electrons generated during glycolysis can be fully utilized in the WL pathway to fix $CO_2$. As a result, the net acetyl-CoA output per glucose molecules increases by 50% in the co-culture and all of the carbon in the sugar substrate is assimilated into usable products. Furthermore, the additional acetate produced by Clj can be re-assimilated by Cac to produce additional butanol in the co-culture system.

Figure 3:
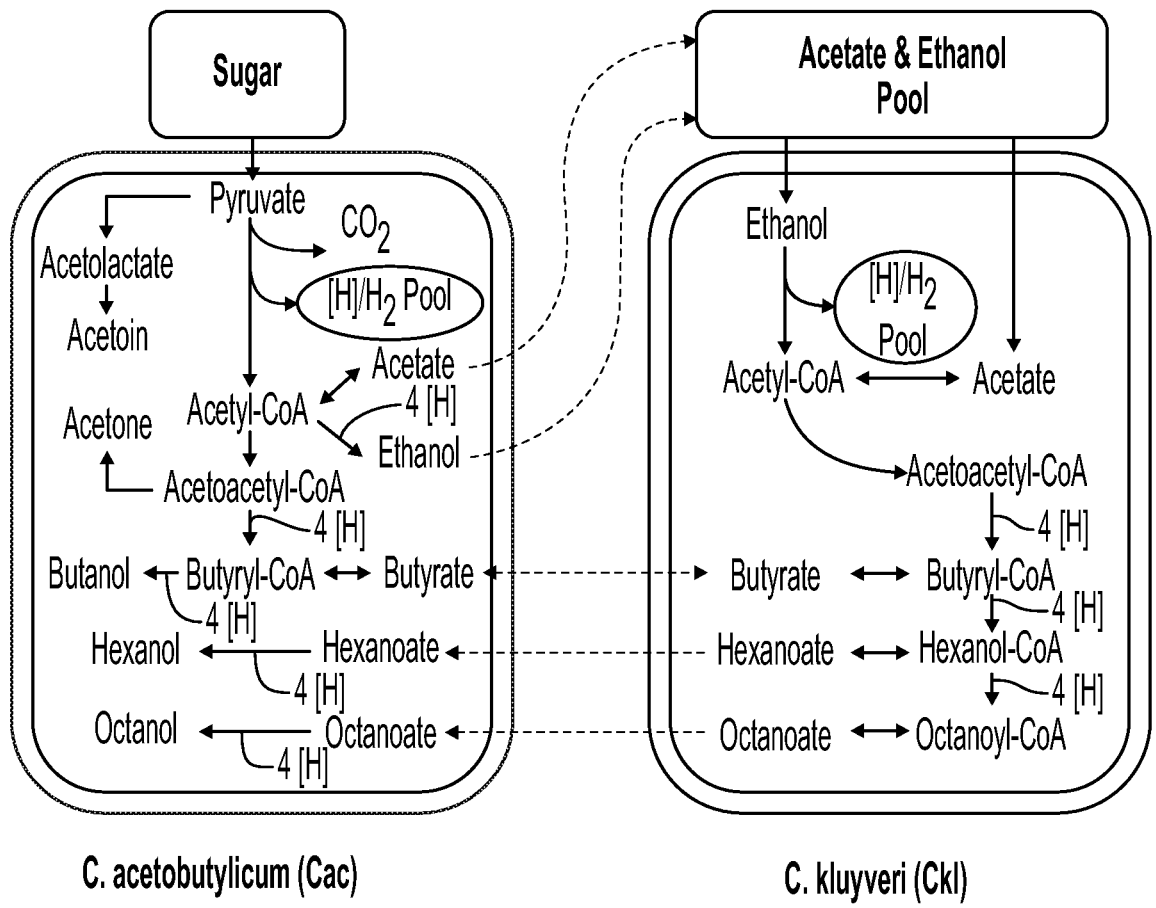
FIG. 3 schematically depicts an overview of the major metabolic pathways found in a co-culture of *C. acetobutylicum* and *C. kluyveri*, the predicted metabolic coupling between both organisms, and a summary of the net yield of electrons and hydrogen ions from the major reactions in each organism.

In another particular embodiment, the syntrophic co-culture according to the present invention comprises a combination of *Clostridium acetobutylicum* and *Clostridium kluyveri* (Ckl). As shown in FIG. 3, primary solventogen Cac is cultured together with another solventogen, Ckl. As described earlier, Cac is able to consume a wide variety of sugar substrates to produce carboxylic acids (acetate and ethanol) and solvents (ethanol, acetone, and butanol). In comparison, Ckl is unable to consume sugars and instead is able consume ethanol and acetate and/or butyrate as substrates. In the process, Ckl is able to perform chain elongation reactions, where acetate (2C) is elongated to produce butyrate (4C), hexanoate (6C), and octanoate (8C). Since ethanol is the only source of energy, Ckl does not have enough reducing power to reduce produced acids to corresponding alcohols. In the Cac/Ckl co-culture, the main feedstock is also a sugar substrate. Here, Cac utilizes the sugar substrate to produce acetate and ethanol, which serve as the substrate for Ckl. Next, Ckl consumes the acetate and ethanol produced by Cac to produce elongated acids, i.e., butyrate, hexanoate, and octanoate. Finally, Cac uses the reducing potential of the sugar substrate to convert all acids produced by Ckl into their corresponding alcohols, i.e., butanol, hexanol, and octanol. The final product mixture is composed of 2C, 4C, 6C and 8C alcohols.

Figure 4:
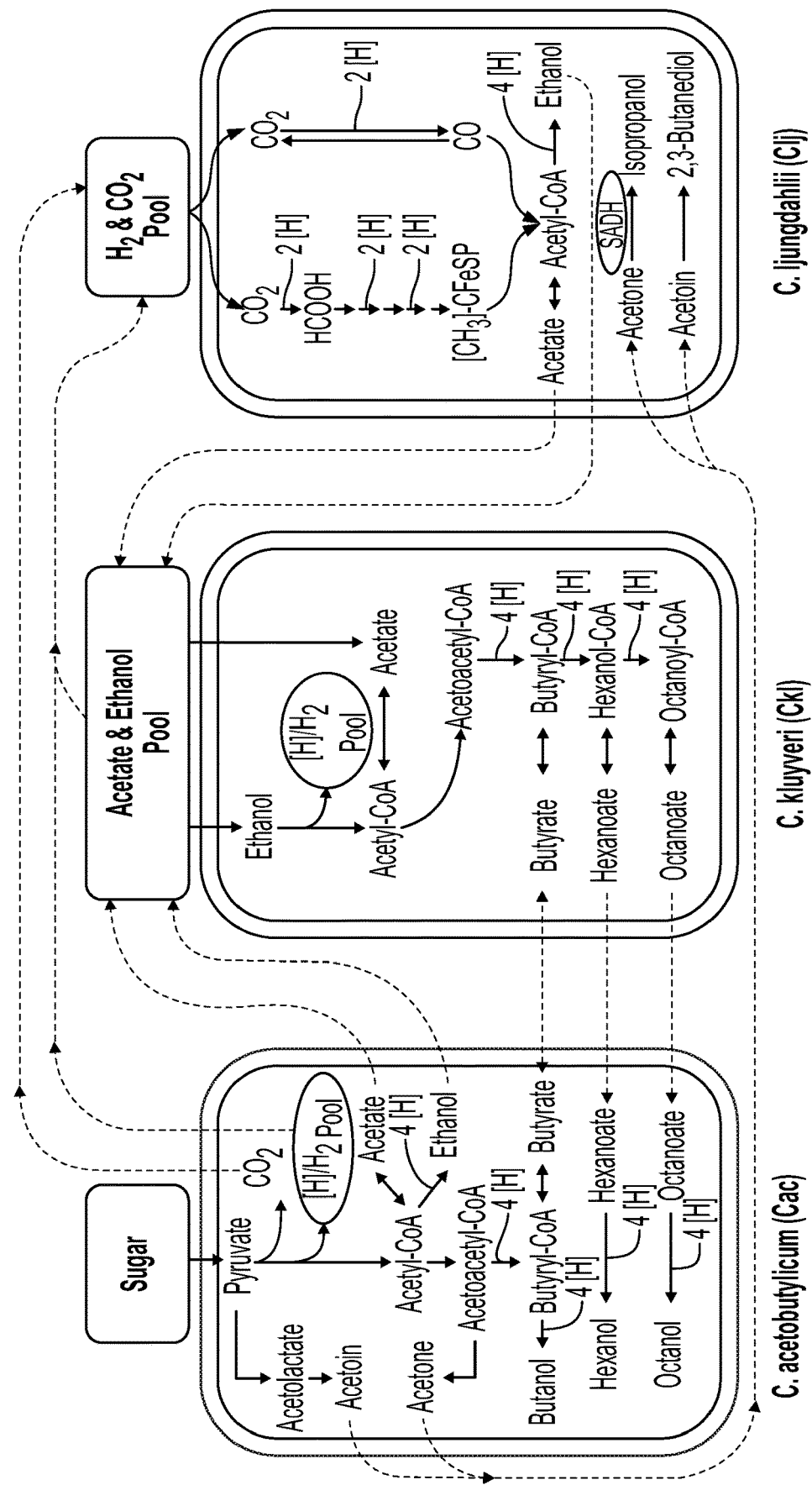
FIG. 4 schematically depicts an overview of the major metabolic pathways found in a co-culture of *C. acetobutylicum*, *C. kluyveri*, and *C. ljungdahlii*, the predicted metabolic coupling between both organisms, and a summary of the net yield of electrons and hydrogen ions from the major reactions in each organism.

In another particular embodiment, the syntrophic co-culture according to the present invention comprises a combination of *Clostridium acetobutylicum*, *Clostridium ljungdahlii*, and *Clostridium kluyveri*. As shown in FIG. 4, the two dual co-cultures described above are combined into a triple co-culture. This system again uses a sugar substrate as the main feedstock. Here, Cac consumes the sugar substrate to produce acids (acetate and butyrate) and solvents (ethanol, acetone, and butanol), as well as $CO_2$ and a large pool of reducing equivalents. Next, Ckl utilizes the acetate, butyrate and ethanol produced by Cac as substrates and converts them to hexanoate and octanoate. At the same time, Ckl generates additional reducing equivalents by converting ethanol to acetyl-CoA. Finally, Clj is able to utilize the $CO_2$ released by Cac and reducing equivalents generated by Cac and Ckl to convert $CO_2$ waste into additional acetate and ethanol. Similar to the Cac/Clj dual co-culture, in this system Clj also reduces acetone and acetoin produced by Cac to isopropanol (2-propanol) and 2,3-butanediol, respectively. As a result, the final product mixture is predominantly composed of alcohols, i.e., isopropanol (3C), 2,3-butanediol (4C), butanol (4C), hexanol (6C), and octanol (8C). Furthermore, due to the $CO_2$ fixing capabilities of Clj, a higher fraction of the sugar substrate is converted to usable products, as compared to the approximately 55% carbon balance of a pure Cac fermentation.

Figure 5:
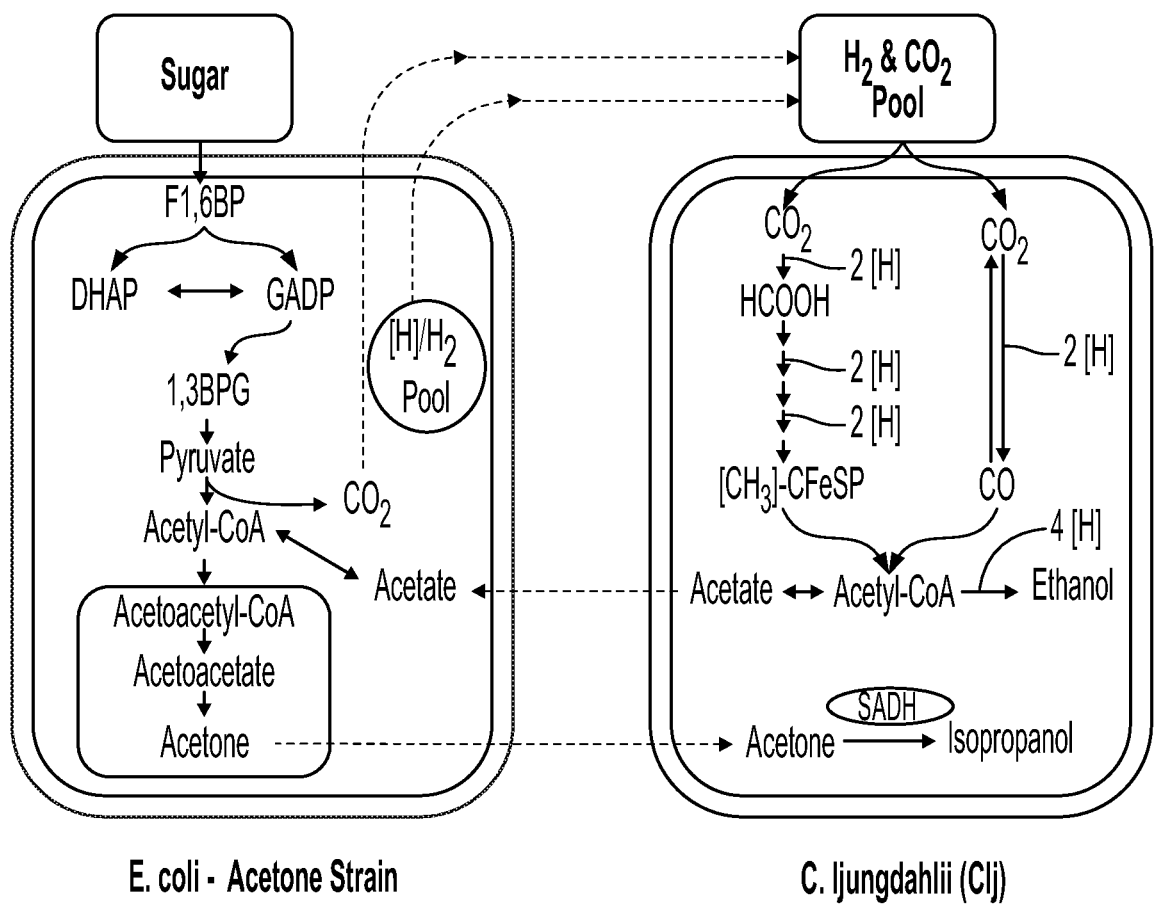
FIG. 5 schematically depicts an overview of the major metabolic pathways found in a co-culture of *E. coli*—Acetone strain and *C. ljungdahlii*, the predicted metabolic coupling between both organisms, and a summary of the net yield of electrons and hydrogen ions from the major reactions in each organism.

In another particular embodiment, the syntrophic co-culture according to the present invention comprises a combination of an acetone-producing strain of *Escherichia coli* (*E. coli*) and *Clostridium ljungdahlii*. As shown in FIG. 5, a strict anaerobe Clj is cultured together with a facultative aerobe *E. coli*. Strict anaerobes like Clj, Cac, and Ckl can only survive in completely anaerobic environments that lack $O_2$. In comparison, facultative aerobes like *E. coli* are capable of growth under aerobic and anaerobic conditions. In the presence of $O_2$, *E. coli* breaks down sugar through the TCA cycle and the oxidative phosphorylation pathways. Under anaerobic conditions *E. coil* can use the glycolysis and pyruvate conversion to acetyl-CoA pathway to generate energy and reducing equivalents. Also, a large genetic toolset has been developed for *E. coli* over the years making it an ideal organism for genetic manipulations. As such, an *E. coli* strain expressing the ctfA, ctfB, and adc genes from *C. acetobutylicum* (Cac), which are responsible for the acetone production, has been developed. Similar to Cac, the acetone-producing *E. coli* strain (EcoA) can break down sugars into acetone, reducing equivalents, and $CO_2$ waste under anaerobic conditions. In order to improve the carbon recovery of the process, EcoA can be cultured together with Clj, which consumes excess reducing equivalents and the $CO_2$ waste generated by EcoA to produce acetate and ethanol. Additionally, Clj reduces volatile acetone produced by EcoA into isopropanol.

In another particular embodiment, the syntrophic co-culture according to the present invention comprises a combination of a first microorganism that metabolizes complex substrates, e.g., lignocellulosic polymers, including toxic substrates (e.g., 2,4,6-trinitrotoluene ("TNT")) and at least one other microorganism that can metabolize metabolites produced by the first microorganism for growth and/or conversion into other useful metabolites the first microorganism cannot produce.

The primary solventogen and the microorganism different from the primary solventogen can be present in the syntrophic co-culture according to the present invention in any suitable ratio. In certain embodiments, the primary solventogen and the microorganism different from the primary solventogen are present in the syntrophic co-culture according to the present invention in a ratio in the range of from 1:1 to 1:20. In certain embodiments, the primary solventogen and the microorganism different from the primary solventogen are present in the syntrophic co-culture according to the present invention in a ratio in the range of from 1:1 to 1:10. Examples of such suitable ratios include, but are not limited to, 1:1, 1:1.5, 1:2, 1:2.5, 1:3, 1:3.5, 1:4, 1:4.5, 1:5, 1:5.5; 1:6, 1:6.5, 1:7, 1:7.5, 1:8, 1:8.5, 1:9, 1.9.5, and 1:10.

In another aspect of the present invention, the present disclosure provides for a method for producing a fermentation product comprising (1) providing the syntrophic co-culture according to the present invention, (2) combining the syntrophic co-culture with at least one biomass component to form a mixture, and (3) fermenting the mixture to provide at least one fermentation product. The at least one fermentation product can be any of the metabolic byproducts described above. As with the further metabolic byproducts, the at least one fermentation product can be an organic molecule useful as a solvent, biofuel, or commodity chemical. In certain embodiments, the method further comprises the addition of exogenous $CO_2$, CO, $H_2$, and mixtures thereof during fermentation of the mixture. Examples of sources of such exogenous gases includes, but is not limited to, syngas produced from the gasification of biomass or other syngas-like processes, pyrolysis of agricultural or municipal wastes, and industrial gas effluents. The composition of the exogenous gas can be controlled in order to maximize the effectiveness of electron and metabolite exchange between the microorganisms to benefit the microorganisms and the fermentation-process outcomes in terms of metabolite yields and selectivity. In certain embodiments, exogenous $H_2$ can be fed to the fermentation process as a secondary substrate (i.e., mixotrophic fermentation of sugars and gasses) to allow for almost complete assimilation of $CO_2$ evolved during sugar breakdown A major drawback of conventional fermentation processes is that the released $CO_2$ accounts for approximately 33 to 40% of all carbon contained in the biomass substrate consumed during fermentation. In contrast, the carbon balance of fermentation processes using the syntrophic co-cultures are higher than those for conventional fermentation processes. As such, mixotrophic fermentation processes using the syntrophic co-cultures according to the present invention produce carbon balances of 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100%.

The following examples are included to demonstrate preferred embodiments. It should be appreciated by those of skill in the art that the techniques disclosed in the examples which follow represent techniques discovered by the inventor to function well in the practice of the products, compositions, and methods described herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLES

Figure 6:
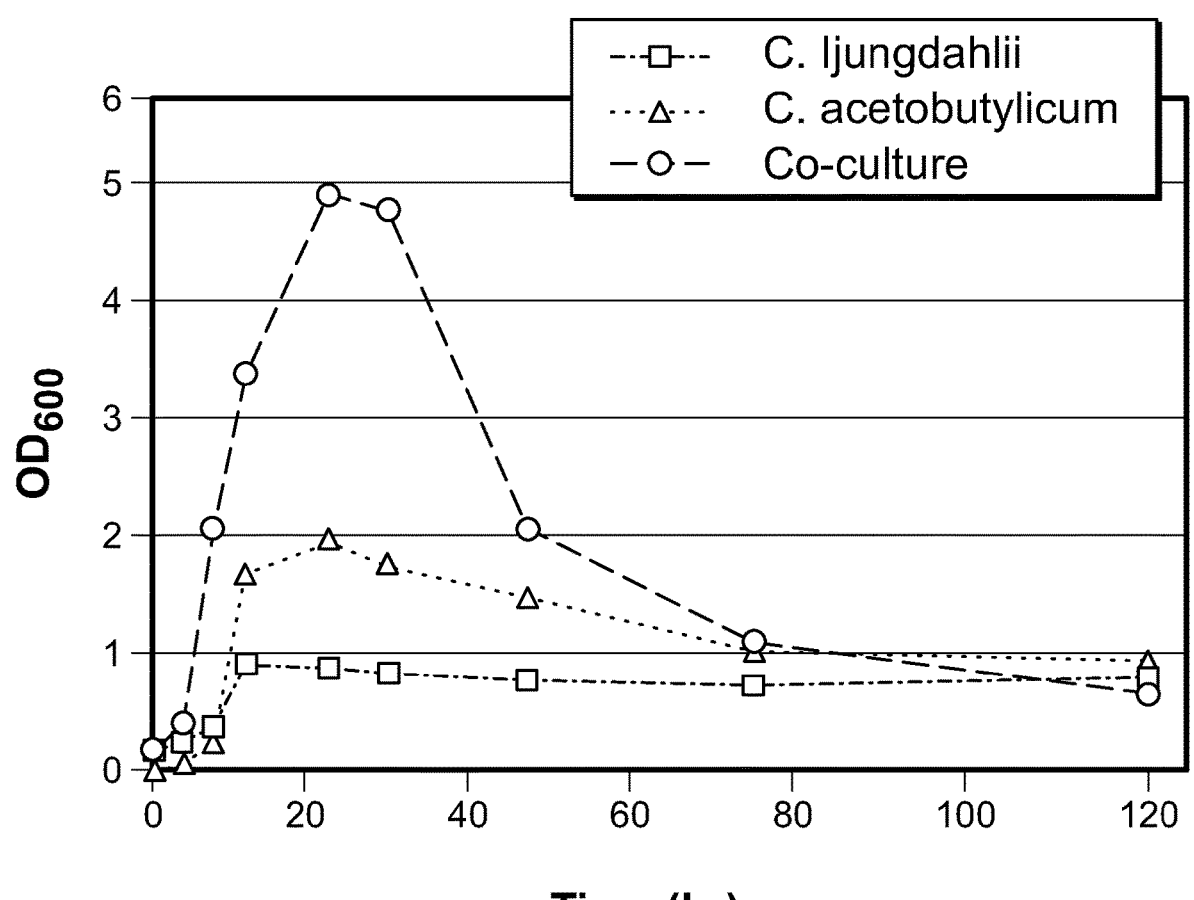
FIG. 6 graphically depicts the optical density profile of the co-culture and monoculture controls of Example 1.

Example 1—Cac-Clj Co-Culture Fermentation Exhibits Different Metabolic Behavior When Compared to Cac and Clj Mono-Culture Systems, Demonstrating the Exchange of Chemicals and Electrons Between the Two Organisms and the Impact of the Syntrophic Relationship All cultures were grown in the same growth medium with 60-80 g/L of glucose, and 5 g/L of fructose. The optical density (OD) was measured using a spectrophotometer at a wavelength of 600 nm. The starting ratio was determined based on the OD of pure seed cultures used to prepare all cultures. The co-culture of Cac and Clj behaved significantly differently from both mono-cultures. First, the co-culture exhibited much better growth compared to mono-culture controls under the same conditions. As shown in FIG. 6, Clj reached an optical density (OD) of 1.0 after approximately 10 hours and remained at the same density for the duration of the experiment. In this particular case, the starting Cac:Clj ratio was 1:30. On the other hand, Cac which is known to grow to higher cell densities than Clj, reached an OD of 2.0 before entering the stationary phase. By comparison, under the same batch growth conditions, the co-culture with a starting Cac:Clj ratio of 1:30 reached a maximum OD of 5.0. Thus, the co-culture reached an OD that was more than twice as high as Cac mono-culture and five times higher than Clj mono-culture. Furthermore, cells in the co-culture formed large clumps in the medium during the initial approximately 48 hours of growth. This behavior was not observed in Cac and Clj monoculture controls. The enhanced growth of the co-culture evidences the metabolic exchange between Cac and Clj.

In the mono-culture system, Clj could only consume the small amount of fructose (5 g/L) that was initially added to the growth medium, since Clj cannot consume glucose and only inert $N_2$ was present in the gaseous headspace. This resulted in the low cell density observed in the Clj mono-culture. In comparison, in the co-culture system, Clj was able to utilize fructose, as well as any $CO_2$ and $H_2$ released by Cac, which lead to better growth. Similarly, Clj had a positive effect on the growth of Cac, as Clj provided Cac with an additional carbon source in the form of acetate produced from $CO_2$ through the WL pathway.

Additional differences between the co-culture and the pure Cac mono-culture were observed in the kinetic profiles of each system. During the fermentation process, Cac and Clj exhibit two metabolic states. Initially, when both organisms are in the exponential growth phase, both will undergo acidogenesis, during which sugars are broken down to produce carboxylic acids, i.e., acetic (Cac and Clj) and butyric (Cac only) acids. The acid production continues until pH in the system drops to approximately 4.5, at which point undissociated acids start to diffuse back into to the cells, where they dissipate the proton gradient. To avoid acid death, low pH triggers cells to switch to the solventogenic phase, during which acids are reassimilated and converted to their respective alcohols (ethanol and butanol) and ketones (acetone and acetoin), while the remaining sugars are converted to alcohols and ketones directly. As a result, Cac mono-cultures will exhibit an increase in acid concentrations at the beginning, followed by a decrease toward the end of the fermentation, as shown in FIG. 7A.

Figure 8:
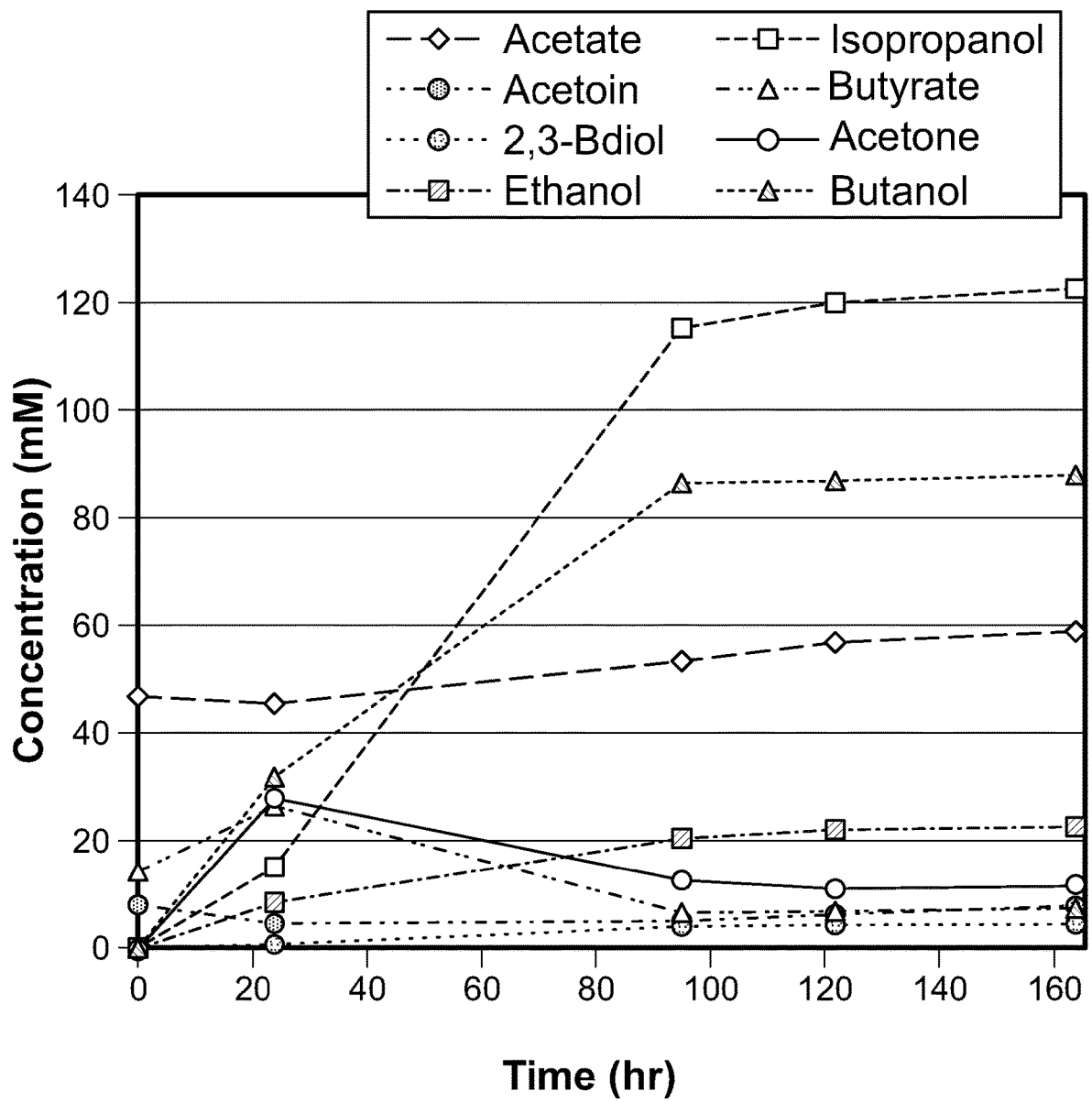
FIG. 8 graphically depicts the change in concentration of major metabolites over the course of the fermentation process in the co-culture system of Example 1.

This was not the case in the co-culture fermentation, as is illustrated in FIG. 8. The concentration of each metabolite was determined using high performance liquid chromatography (HPLC). In this particular co-culture fermentation, the starting Cac:Clj ratio was 1:5. The growth medium contained 60 g/L of glucose and 5 g/L of fructose. In the co-culture, the concentrations of butyrate, ethanol, and butanol did follow the expected behavior, where butyrate exhibited an initial increase and was later reassimilated, while ethanol and butanol concentrations increased throughout the fermentation. In comparison to butyrate, acetate concentration remained relatively constant throughout the entire process at 50 mM. This behavior further evidences the metabolic coupling between Cac and Clj in the co-culture. Clj was able to produce extra acetate from $CO_2$ using the WL pathway, which increased the acetate pool in the system. At the same time, Cac consumed acetate at a similar rate to produce additional ethanol and butanol. Similar rates of acetate production by Clj and acetate consumption by Cac maintained acetate at a constant level throughout the fermentation. This data demonstrates not only that the two types of cell exchange metabolite chemicals to enhance their survival and growth, but also that electrons are also exchanged to achieve that goal.

Figure 7:
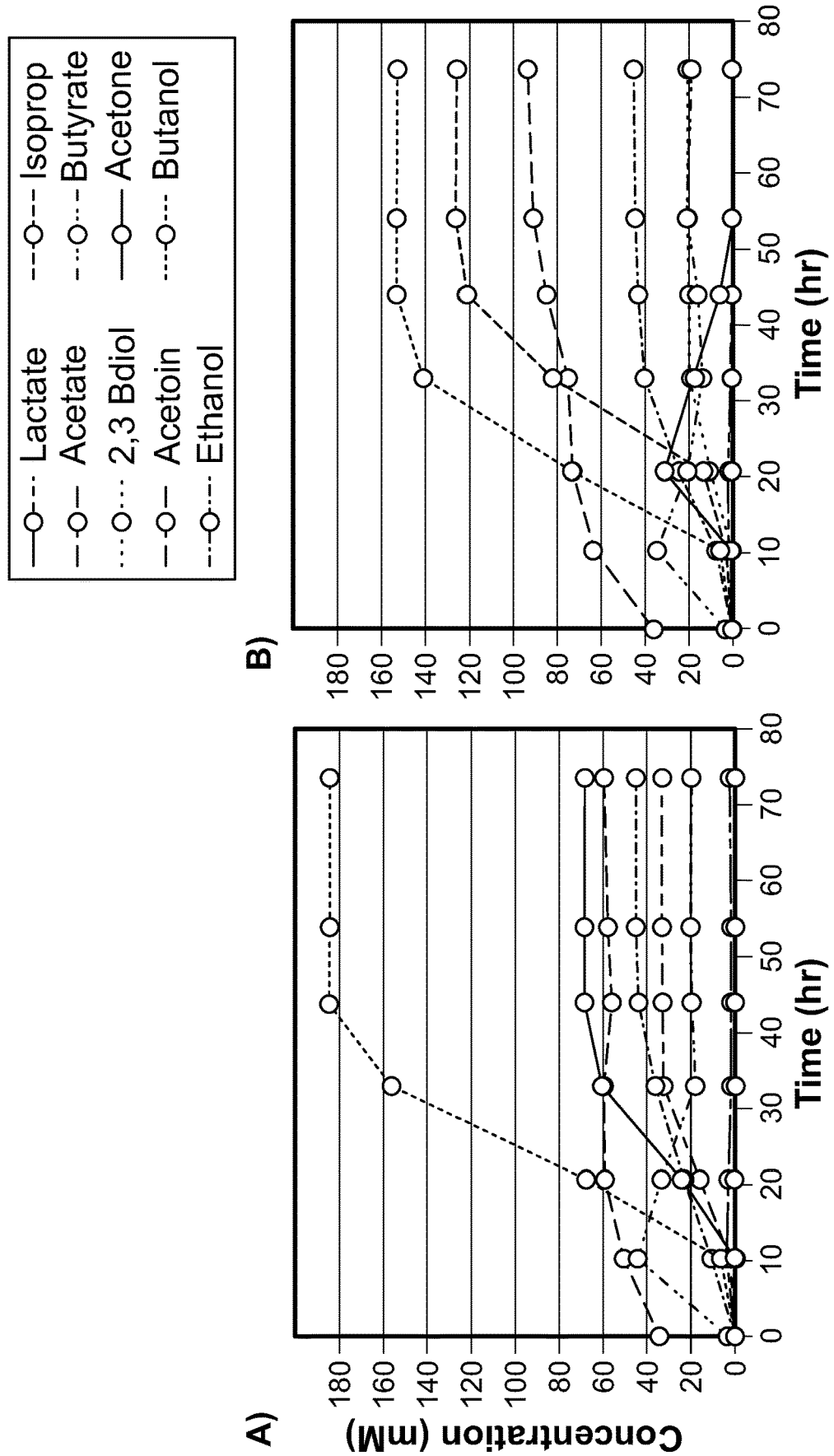
FIG. 7A graphically depicts a temporal metabolite profile of a representative example of pure *C. acetobutylicum* (Cac) mono-culture of Example 1.
FIG. 7B graphically depicts a temporal metabolite profile of a representative example of *C. acetobutylicum* (Cac)—*C. ljungdahlii* (Clj) co-culture with a starting *C. ljungdahlii* (Clj):*C. acetobutylicum* (Cac) ratio of 10 of Example 1.

Similar behavior was observed in a subsequent experiment where the growth medium contained 80 g/L of glucose and 5 g/L of fructose, as shown in FIG. 7B. First, acetate concentration continued to increase in the co-culture system during the entire fermentation period. Second, butyrate concentration began to increase again after 40 hours of fermentation, which was not observed in the pure Cac control. Third, acetone accumulated to 35 mM in the co-culture before it was completely consumed and reassimilated into 2-propanol. Finally, acetoin was not detected at any point in the co-culture and was immediately converted into 2,3-butanediol.

Again, this behavior further evidences the metabolic coupling between Cac and Clj in the co-culture. Since the only substrate available in the medium was glucose, which Clj cannot metabolize, the continuous production of acetate was the result of Clj consuming $CO_2$ and $H_2$ waste released by Cac. Furthermore, acetone was quickly removed from the system by Clj and converted to 2-propanol. The product removal stimulated the acetone pathway to produce more, which diverted carbon away from the butanol pathway (so that a lower butanol titer was observed in the co-culture) and stimulated additional butyrate production late in the fermentation process. These results demonstrate that Cac and Clj are able to exchange both metabolites and electrons (or reducing equivalents) in the co-culture system.

Figure 9:
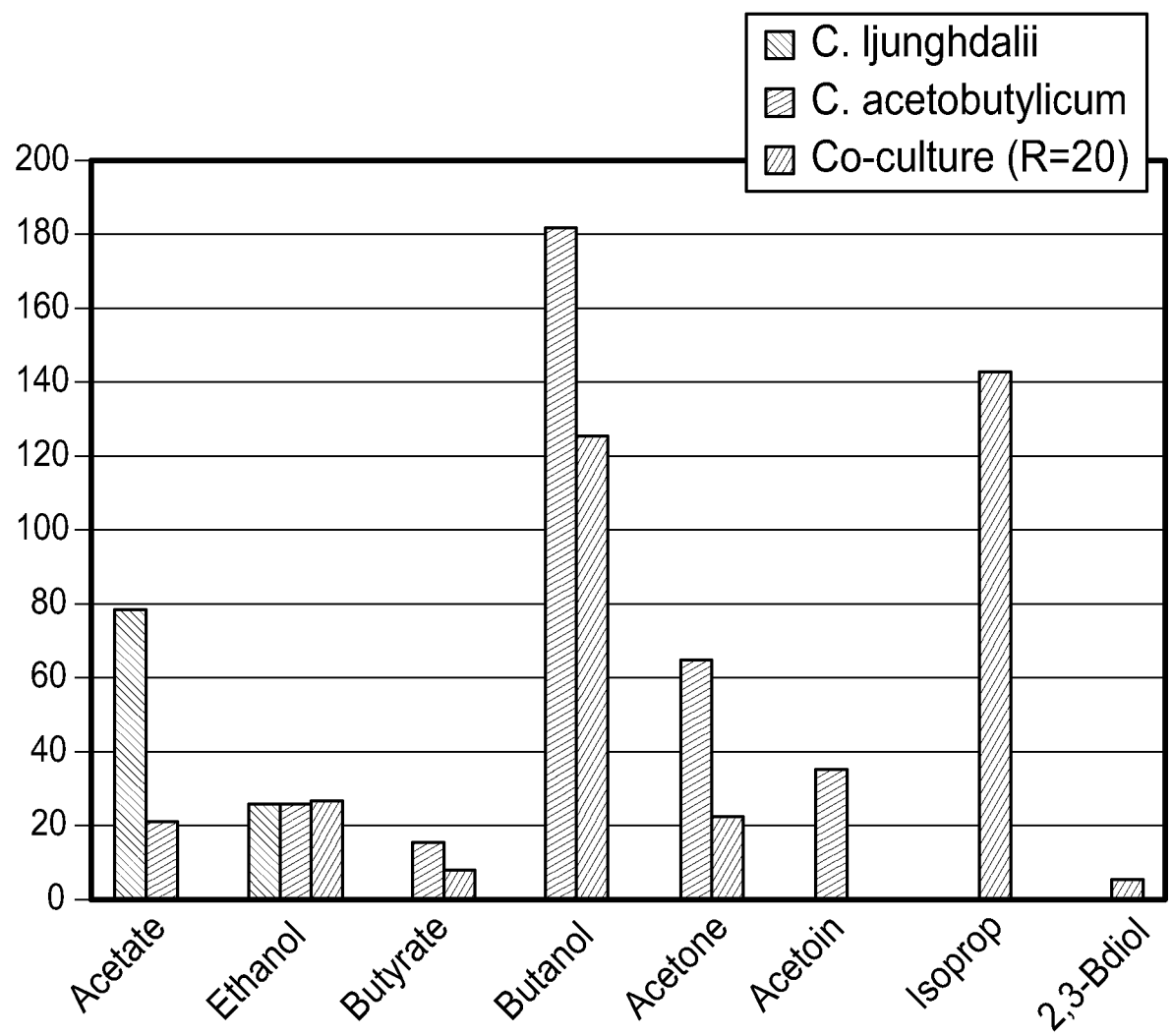
FIG. 9 graphically depicts a comparison of the net metabolite production between the co-culture system and mono-cultures of *C. acetobutylicum* and *C. ljungdahlii* of Example 1.

FIG. 9 summarizes the net metabolite production in mono-cultures and the co-culture. All cultures were grown in sealed serum bottles with 30 mL of growth medium and were flushed with pure $N_2$. All cultures were grown on sugar substrate only, in the form of 60 g/L of glucose and 5 g/L of fructose. Both mono-cultures behaved as expected. Clj produced 70 mM acetate and 30 mM ethanol. On the other hand, Cac produced 180 mM butanol, 65 mM acetone, 25 mM ethanol, and 30 mM acetoin, and reassimilated almost all acids, i.e., acetate and butyrate. The high butanol-to-ethanol ratio is characteristic for Cac mono-cultures.

In comparison, the Cac-Clj co-culture produced 125 mM of butanol, 25 mM of ethanol, and 22 mM of acetone. Furthermore, the production of acetone and acetoin appear to be suppressed in the co-culture when compared to Cac mono-culture. Instead, the co-culture produced 142 mM of isopropanol and 5 mM of 2,3-butanediol. The kinetic profiles of the co-culture system (FIGS. 7B and 8) showed that acetone levels initially reached a concentration of 30 mM before it began to decrease. Based on the chemical structure, the co-culture system was able to reduce 3C acetone (2-propanone) into 3C isopropanol (2-propanol). The removal of acetone from the system stimulated the acetone pathway in Cac to produce additional acetone, which resulted in high final concentration of isopropanol in the co-culture. The same was true for 4C acetoin (3-hydroxy-2-butanone) which was reduced in the co-culture to 2,3-butanediol. The conversion of acetoin to 2,3-butanediol was faster, as no acetoin was detected in the co-culture system.

Figure 10:
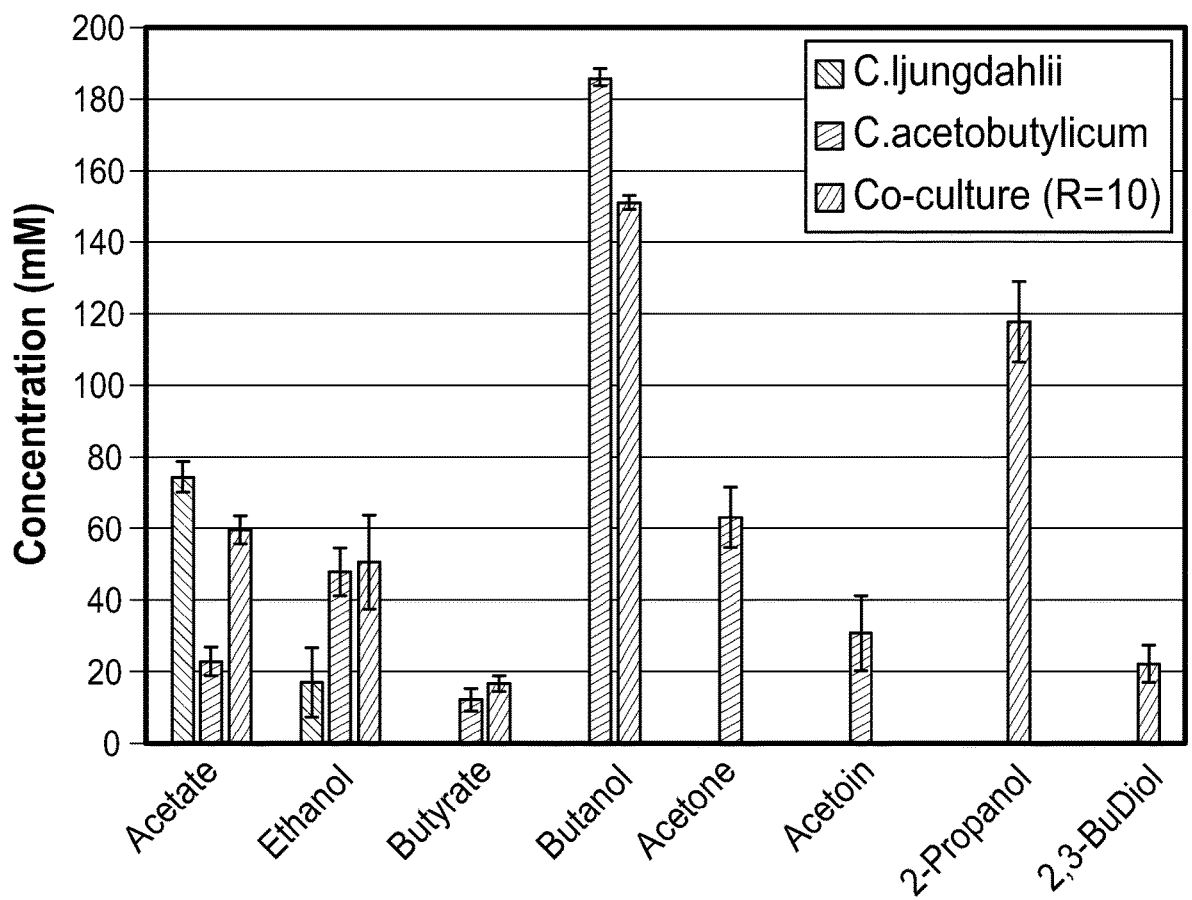
FIG. 10 graphically depicts a comparison of the net metabolite production between a *C. acetobutylicum*—*C. ljungdahlii* co-culture and *C. acetobutylicum* and *C. ljungdahlii* mono-cultures of Example 1.

A subsequent experiment with the growth medium containing 80 g/L of glucose and 5 g/L of fructose is summarized in FIG. 10. There, the Clj control produced 74 mM of acetate, and 19 mM of ethanol, while the Cac control produced 185 mM of butanol, 62 mM of acetone, 30 mM of acetoin, 50 mM of ethanol, as well as some acetate and butyrate. In comparison, the Cac-Clj co-culture also produced butanol (155 mM) and ethanol (52 mM). Again no acetone or acetoin were found in the co-culture. Instead, the co-culture system was found to have produced 119 mM of 2-propanol and 22 mM of 2,3-butanediol.

In the case of 2,3-butanediol, Clj has been reported to express the pyruvate:ferredoxin oxidoreductase (PFOR) enzyme, which is able to convert 2C acetyl-CoA (produced from $CO_2$ and $H_2$) to 3C pyruvate. Next, two pyruvate molecules are condensed together to form one 4C acetoin. Finally, acetoin is reduced to 2,3-butanediol through the action of the 2,3-butanediol dehydrogenase (23BDH) and the secondary alcohol dehydrogenase (SADH). Clj mono-cultures have been reported to produce approximately 2 mM of 2,3-butaneidol, which is 10-fold lower compared to the 22 mM titer observed in the Cac-Clj co-culture system. Without being bound by theory, the higher titers observed in the co-culture appear to have been the result of acetoin production by Cac, which was then reduced to 2,3-butanediol by Clj in the co-culture system.

The production of 2-propanol in the co-culture was more surprising, as neither Cac nor Clj are able to produce it on their own. Without being bound by theory, the production of 2-propanol appears to have been the result of syntrophic interactions between Cac and Clj in the co-culture, where Cac produces acetone from the sugar substrate, and Clj reduces acetone to 2-propanol using the promiscuous SADH enzyme, and electrons (or reducing equivalents) generated by Cac.

Figure 11:
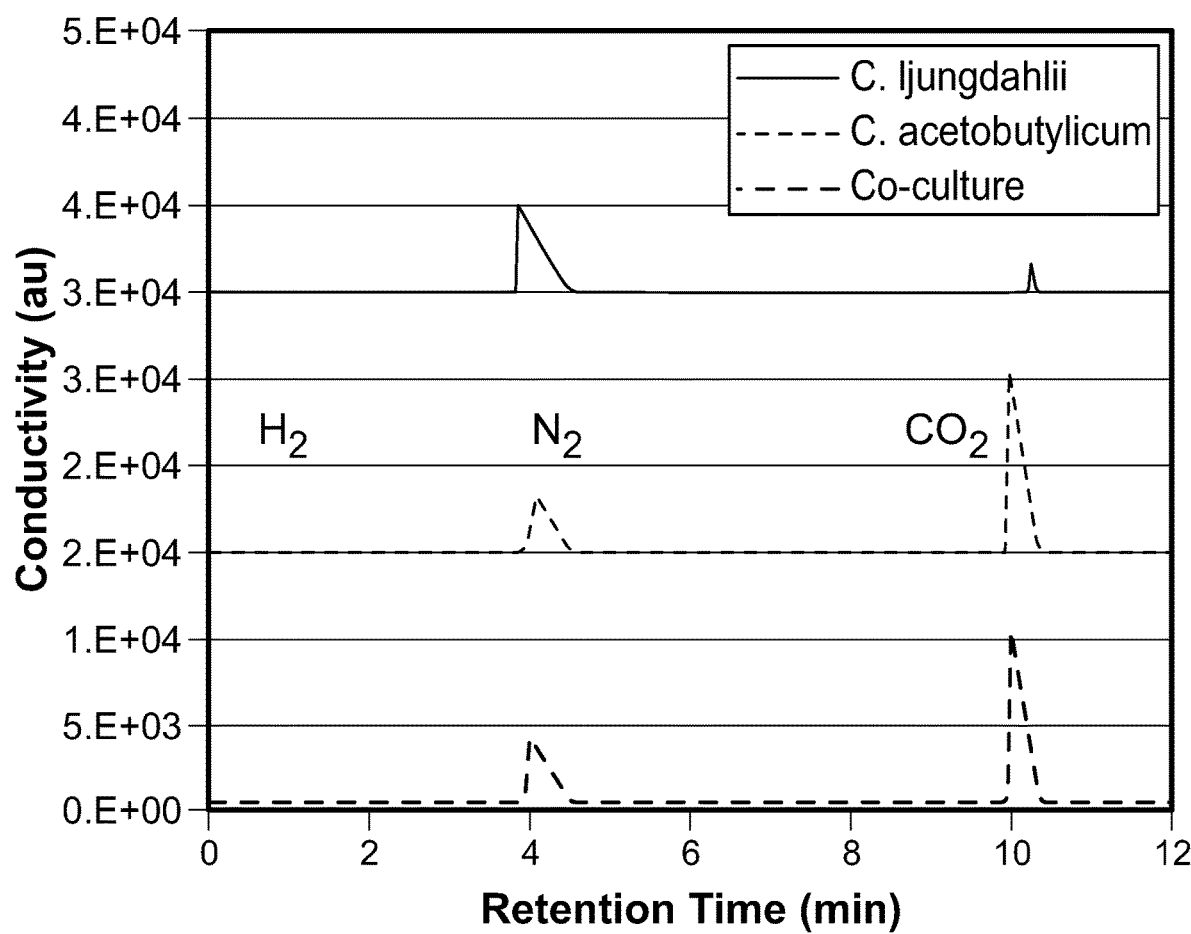
FIG. 11 graphically depicts the final gas composition of the co-culture and monoculture systems of Example 2.

Example 2—Composition Analysis of Gasses Evolved During Fermentation Support the Metabolic Coupling Between Both Species in the Co-Culture System The observed metabolite profile in the co-culture is consistent with the gas headspace composition analysis shown in FIG. 11. All three cultures were grown in sealed 160 mL serum bottles with 30 ml of liquid culture. The growth medium contained 30 g/L of glucose and 5 g/L of fructose. The gas composition was evaluated using gas chromatography (GC) which detects gases based on their thermal conductivity. The thermal conductivity of each gas was evaluated with respect to the helium carrier gas. The $N_2$ and $CO_2$ peaks are positive in the chromatogram because their thermal conductivity is higher than that of helium carrier gas, while the $H_2$ peak is negative as a result of a low thermal conductivity. The relative peak size does not directly correlate with the mole fraction of each gas in the mixture. At the start of the experiment all cultures were flushed with pure $N_2$. As a result, all three cultures had a peak corresponding to $N_2$. *C. ljungdahlii produced small amount of $CO_2$* from consumption of fructose, while *C. acetobutylicum* produced $H_2$ and $CO_2$. In comparison, the co-culture had $CO_2$ but no $H_2$ present in the system.

All cultures started with a pure $N_2$ atmosphere. Clj mono-culture produced a small amount of $CO_2$ during fructose consumption. Cac mono-culture produced $CO_2$ and $H_2$. The production of $H_2$ by Cac was carried out by hydrogenase enzymes, which convert any excess reducing equivalents into $H_2$ gas. In comparison, the final gas mixture in the co-culture system contained $CO_2$, but no $H_2$. Therefore, the co-culture was able to utilize the entire pool of reducing equivalents to produce alcohols (i.e., ethanol and butanol). As a result, Clj was able to utilize electrons produced by Cac during glycolysis to re-assimilate some of the $CO_2$ released by Cac. The gas composition analysis is consistent with the pressure profiles of the co-culture and mono-culture controls.

Figure 12:
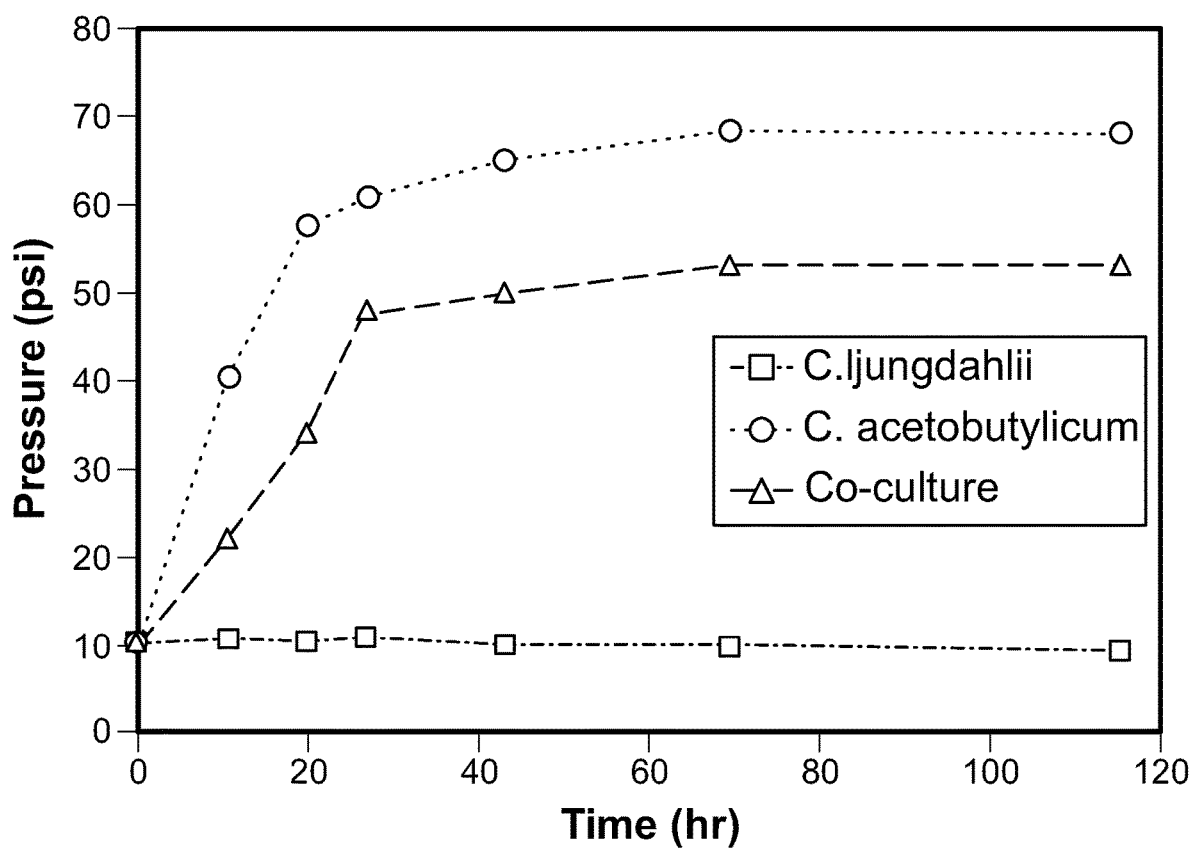
FIG. 12 graphically depicts the pressure profiles (In terms of gauge pressure) in the co-culture and the *C. acetobutylicum* and *C. ljungdahii* mono-culture controls of Example 2.

FIG. 12 summarizes the gauge pressure over time in each culture. All cultures were grown in sealed 160 mL serum vials with 30 mL of liquid culture. The growth medium contained 30 g/L of glucose and 5 g/L of fructose. Initially, all bottles were pressurized to 10 psig with pure $N_2$. No pressure change was observed in the Clj mono-culture because the medium was supplemented with 5 g/L of fructose, and no exogenous gasses that Clj could consume. In comparison, the pressure in Cac mono-culture increased to 70 psig due to glucose consumption by Cac. Finally, the co-culture reached a final pressure of 53 psig. Thus, the co-culture was able to consume part of the CO2 released by Cac. In the Clj monoculture, the pressure remained constant since the medium was supplemented with only 5 g/L of fructose and inert $N_2$ in the headspace. In the Cac monoculture, the pressure reached 70 psig as Cac consumed 15 g/L of 30 g/L of glucose available in the system. In comparison, the co-culture reached a lower final pressure of 53 psig and consumed all of 30 g/L of glucose initially added to the growth medium. Thus, the Clj in the co-culture must have consumed $CO_2$ released by Cac in order to reach a lower final pressure than the Cac mono-culture.

Based on previous theoretical analysis, in order to fully re-assimilate all of $CO_2$ evolved during the sugar consumption, the co-culture system must be supplied with exogenous syngas (i.e., a mixture of $H_2$ and CO) to increase the pool of free electrons that are available for $CO_2$ fixation. Furthermore, increasing the amount of available electrons will improve the final butanol production, since the conversion of acetyl-CoA to butanol requires 8 electrons per butanol molecule, compared to 4 electrons needed per ethanol molecule. As shown in FIG. 1, biomass could be used as a source of sugar and gas feed, since hemicellulose and cellulose can be digested by various clostridia, while any remaining undigested biomass can be converted to a syngas mixture through chemical means, such as the gasification process.

Furthermore, with a large enough supply of syngas, exogenous $CO_2$ could be utilized together with the $CO_2$ evolved during the sugar breakdown to produce biofuels, such as butanol, as well as other commodity chemicals.

Example 3—Effect of Starting Cac:Clj Ratio on Alcohol Production in the Co-Culture One of the factors that affect the performance of the co-culture system is the starting ratio of Cac to Clj. As discussed above, Cac grows at least twice as fast as Clj and reaches much higher cell densities under the same growth conditions. Furthermore, both organisms are likely to exhibit different rates of substrate utilization and product formation. Therefore, there must exist an optimal ratio of both cell populations, at which point the overall rate of production of $CO_2$ by Cac will match the rate of $CO_2$ consumption by Clj. Similar considerations can be made for the electron and acetate exchange between both cells in the co-culture. Starting Cac:Clj ratios of 1:50, 1:30, 1:20, 1:10, 1:5, 1:2.5, and 1:1 were tested to ensure that there was an excess of Clj cells in the system due to its slower growth rate. All co-cultures were prepared with pure Cac and Clj seed cultures whose optical densities ($OD_{600}$), hereinafter "ODs," ranged between 0.40-0.60 to ensure both organisms were in the exponential growth phase. OD was treated as a measure of cell concentration in order to determine the appropriate volume of each seed culture used to prepare the co-culture.

Figure 13:
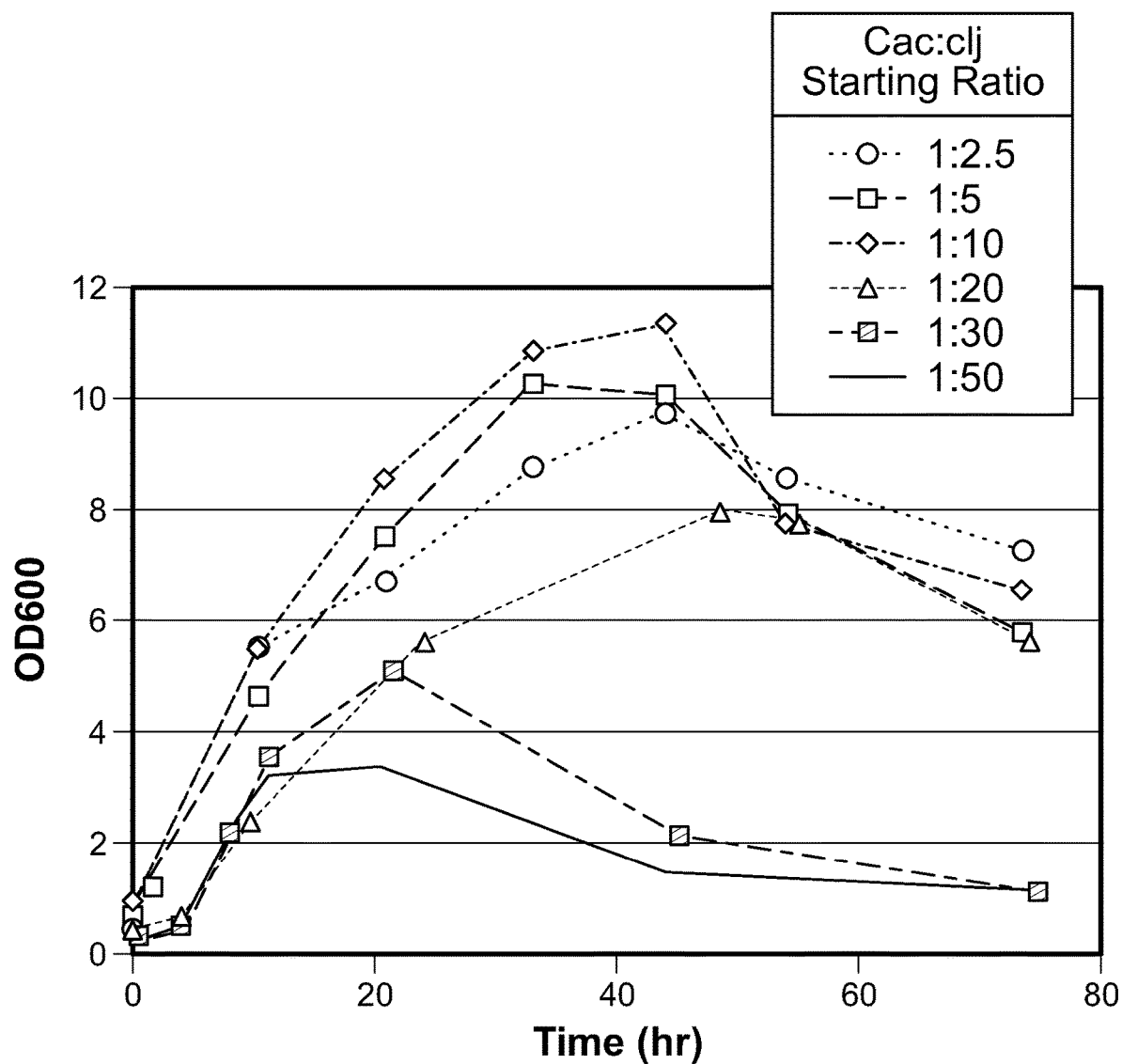
FIG. 13 graphically depicts the optical density (OD) profile of co-culture fermentations with different starting *C. acetobutylicum*:*C. ljungdahlii* ratios of 1:20, 1:10, 1:5 and 1:2.5 of Example 3.

FIG. 13 illustrates the OD profiles of co-cultures with starting ratios ranging from 1:50 to 1:2.5. Optical density measurements were carried out using a spectrophotometer at a wavelength of 600 nm. All systems with ratios 1:2.5-1:20 exhibited higher OD levels compared to co-culture system with the starting ratio of 1:30 and 1:50. The 1:2.5, 1:5, and 1:10 co-cultures reached the highest ODs in the range 10.0-11.0, followed by 1:20 co-culture with OD of 8.0, and 1:30 co-culture with OD of 5.0. The 1:50 co-culture performed the poorest with a maximum OD of 3.5. Overall, cell densities in the co-cultures with starting ratios of 1:20 and up were higher compared to co-cultures with starting ratios of 1:30 and 1:50.

Figure 14:
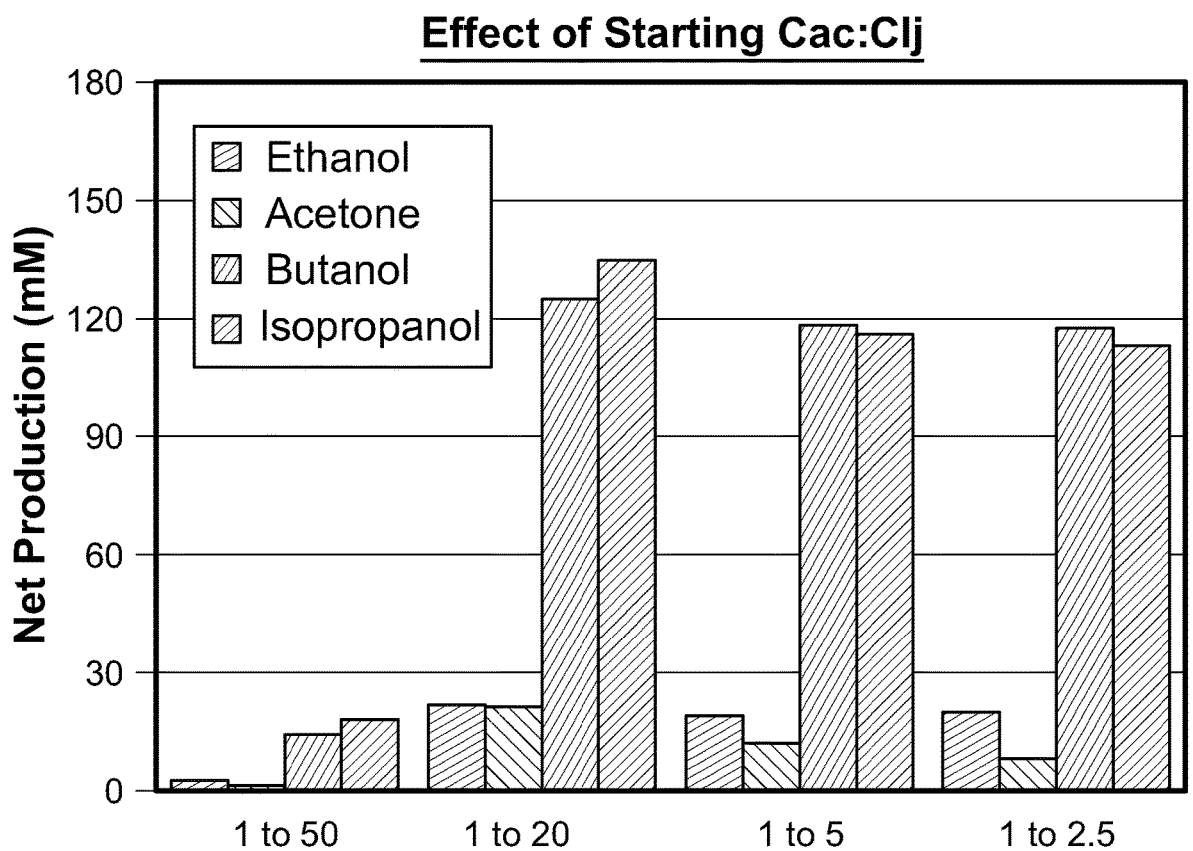
FIG. 14 graphically depicts the effect of the starting *C. acetobutylicum*:*C. ljungdahii* ratio in the co-culture on solvent production (mM) of Example 3.

In order to quantify the co-culture performance more accurately, the net alcohol production (i.e., ethanol, butanol, and isopropanol) was determined for each system, as illustrated in FIG. 14. The tested ratios ranged from 1:50 to 1:2.5. The lowest ratio of 1:50 produced the least solvents with 20 mM of isopropanol, 15 mM butanol and 2 mM ethanol. In comparison, ratios of 1:20 and higher produced up to 140 mM of isopropanol, 125 mM butanol, and 25 mM of ethanol. No clear trend was observed in alcohol production among Cac:Clj ratios lower than 50. The co-culture with the starting ratio of 1:50 produced the least amount of solvents, which is consistent with the observed low cell density in that system. Decreasing the ratio to 1:20 significantly increased the alcohol production to 140 mM isopropanol, 125 mM butanol, and 25 mM of ethanol. Once the ratio was decreased below 1:20 the solvent production did not improve any further. This was the result of the opposing effects of the limited pool of the reducing equivalents, and size of the Clj population. At a high Cac:Clj ratio of 1:50, the population of Cac in the co-culture was too small relative to Clj population to produce enough reducing equivalents for all Clj cells present in the system. When the ratio decreased to 1:20, the population of both organisms approached an optimum where Cac population was large enough to supply all available Clj cells with electrons for WL pathway. As the ratio continued to decrease, the relative size of Clj population to Cac population was too small to produce any significant changes to the overall metabolite profile of the co-culture. Therefore, the optimal starting Cac:Clj ratio in the co-culture was found to be 1:20.

Figure 15:
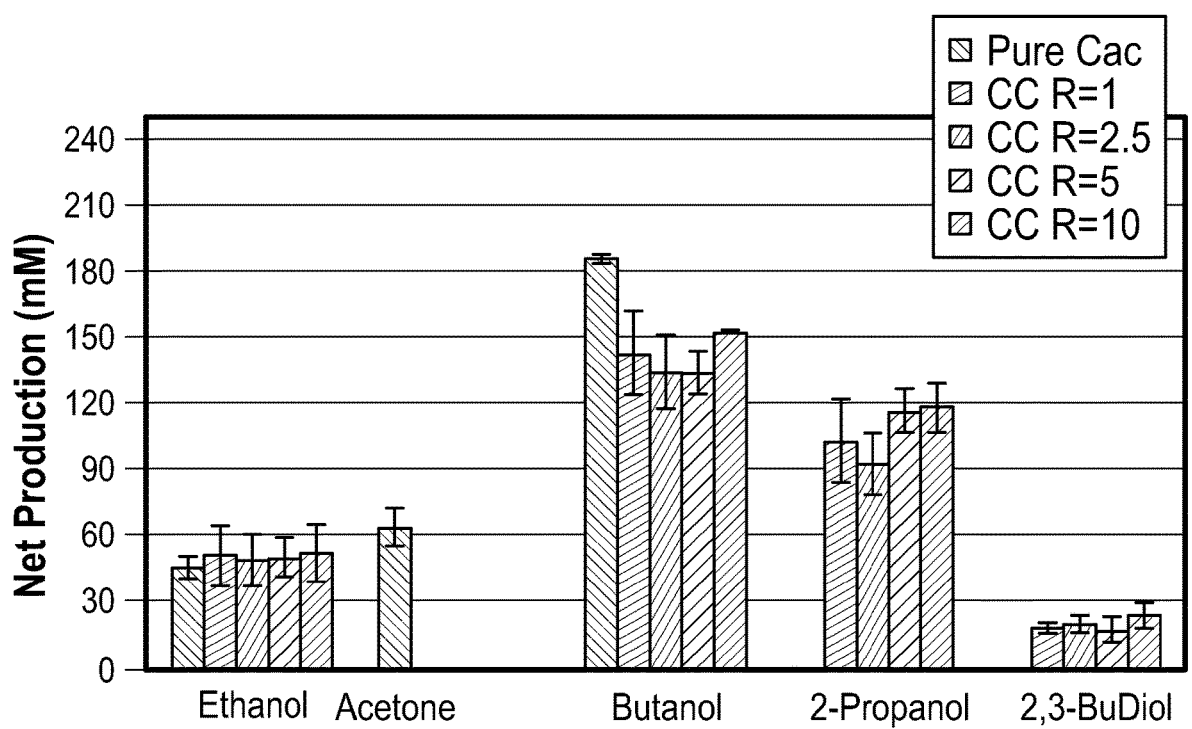
FIG. 15 graphically depicts the net solvent production (mM) in the pure *C. acetobutylicum* control and various tested co-culture systems (R=1 to R=10) of Example 3.

As shown in FIG. 15, the butanol titer in the co-cultures with starting Cac: Clj ratios of 1:10, 1:5, 1:2.5, and 1:1 was lower with an average of 145 mM, compared to 180 mM produced by pure Cac. In the case of acetone, none was present in any of the co-cultures. Instead, co-cultures produced 110 mM of 2-propanol on average. The 2-propanol titer in all co-cultures was almost 2-fold higher than acetone titer in pure Cac control. Without being bound be theory, the removal of acetone by Clj in the co-culture stimulated the acetone pathway, which diverted carbon away from butanol pathway, and resulted in improved acetone/2-propanol production and lower butanol titers in the co-culture, relative to pure Cac control. Overall, the co-culture was able to reduce all ketone byproducts, like acetone and acetoin, to less volatile alcohol products. Finally, co-cultures with various R-ratios were found to exhibit similar performances, which demonstrates the robustness of the Cac-Clj co-culture system.

Carbon recovery was then determined for each of the co-cultures with starting Cac:Clj ratios of 1:10, 1:5, 1:2.5, and 1:1. Carbon recovery is defined as the ratio of the amount of carbon found in all products (here, acetate, butyrate, ethanol, butanol, acetone, 2-propanol, acetoin, and 2,3-butanediol) and the amount of carbon in consumed sugar (here, glucose). The upper limit for the carbon recovery of any fermentation process where organic compounds are broken down to acetyl-CoA is 66% due to decarboxylation of pyruvate to form acetyl-CoA.

Figure 16:
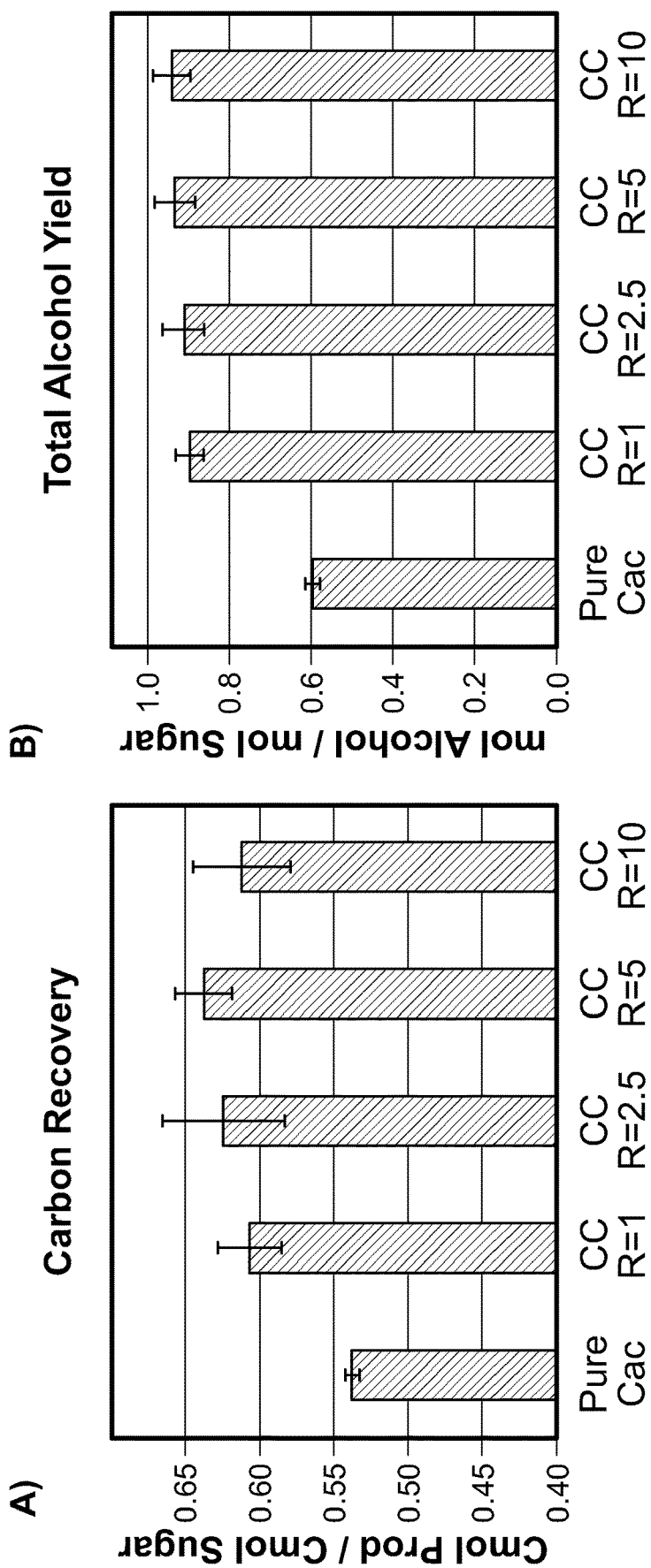
FIG. 16A graphically depicts the carbon recovery in the pure *C. acetobutylicum* control and various tested co-culture systems (R=1 to R=10) in Example 3.
FIG. 16B graphically depicts the total alcohol yield per mole of sugar consumed in the pure *C. acetobutylicum* control and various tested co-culture systems (R=1 to R=10) in Example 3.

As summarized in FIG. 16A, the carbon recovery of pure Cac fermentation was found to be 54% due to additional decarboxylation reactions that occur during acetone and acetoin synthesis. In comparison, all tested co-cultures had a carbon recovery of 60% to 65%. The higher carbon recovery observed in co-cultures was the result of $CO_2$ waste fixation by Clj. Finally, the total alcohol yield was determined for each system. The pure Cac fermentation produces both alcohols (ethanol and butanol) and ketones (acetone and acetoin). The ketone production can be problematic, especially in fuel applications, due to the higher volatility of ketone compounds, compared to alcohols with the same carbon content. As shown in FIG. 16B, the total alcohol yield (including ethanol, butanol, 2-propanol, and 2,3-butanediol) was 0.9 mol/mol of glucose, compared to 0.6 mol/mol of glucose yield in pure Cac control. The higher alcohol yield in the co-culture resulted from Clj's ability to utilize excess reducing equivalents generated by Cac to reduce ketones (i.e., acetone and acetoin) into their respective alcohols (i.e., 2-propanol and 2,3-butanediol). To summarize, the Cac-Clj co-culture generates a product stream composed of alcohols with small amounts of unreacted carboxylic acids.

Figure 17:
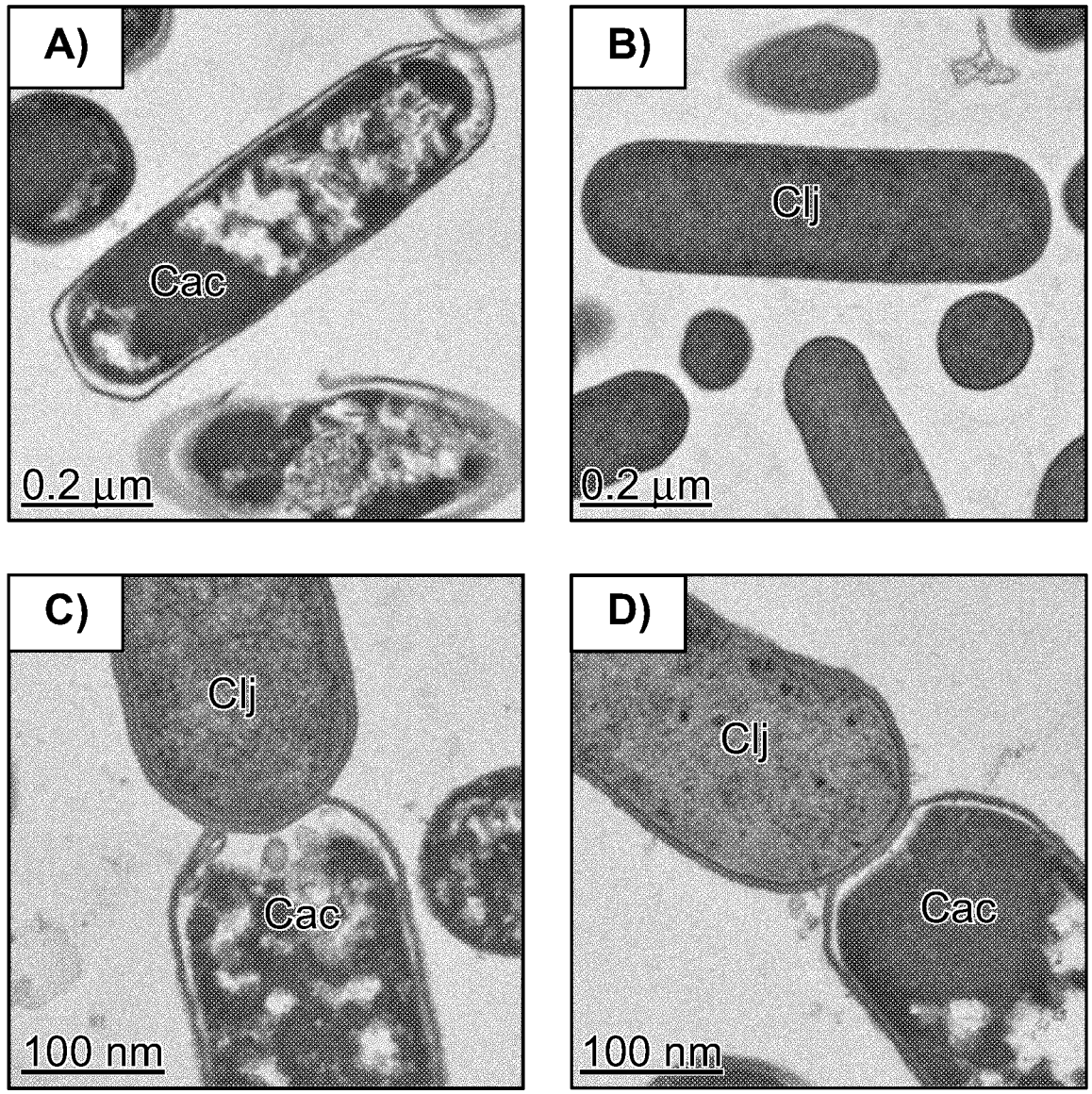
FIG. 17A illustrates a *C. acetobutylicum* mono-culture after 24 hours of incubation when it begins to form granulose (Example 4).
FIG. 17B illustrates a *C. ljungdahlii* mono-culture after 48 hours of incubation (Example 4).
FIG. 17C illustrates *C. ljungdahlii* and *C. acetobutylicum* with their membranes fused together as a result of being cultured together (Example 4).
FIG. 17D illustrates *C. ljungdahlii* and *C. acetobutylicum* with their membranes fused together as a result of being cultured together (Example 4).

Example 4—Cac and Clj Grown in the Co-Culture System Interact Through Membrane Fusion Aiming to Facilitate and Optimize the Exchange of Chemicals and Electrons As described in Examples 1 and 3, cells in the co-culture exhibited the formation of large clumps. Thus, the physical interaction between Cac and Clj was examined in the co-culture system using transmission electron microscopy (TEM), as illustrated in FIG. 17. Images were produced using transmission electron microscope (TEM). Initially both cells were indistinguishable. FIG. 17A shows a *C. acetobutylicum* mono-culture after 24 hours of incubation when it begins to form granulose. FIG. 17B shows *C. ljungdahlii* mono-culture after 48 hours of incubation; *C. ljungdahlii* did not differentiate during that period. Panels C and D show images of the co-culture. Cells resembling *C. ljungdahlii* and *C. acetobutylicum* were observed in the co-culture. Furthermore, *C. ljungdahlii* and *C. acetobutylicum* appear to fuse their membranes when cultured together, as shown in FIG. 17C and FIG. 17D. This behavior was not observed mono-cultures of both cells.

First, the cell structure of Cac and Clj mono-cultures was examined. Initially, both cells were indistinguishable and resembled Clj cells, as shown in FIG. 17B. After 24 hours of incubation, Cac mono-culture initiated its sporulation process, which coincides with cells' shift to solventogenesis. As part of the sporulation process, a starch-like storage compound named granulose is formed in the cytoplasm. The granulose appears translucent (white) on TEM images, as shown in FIG. 17A. In comparison, Clj mono-culture did not show any signs of differentiation or sporulation even after 48 hours of incubation.

Next, the Cac-Clj co-culture was visualized using the same method. After 24 hours of incubation, the co-culture contained cells that structurally resembled cells from Cac (Indicated by the presence of granulose) and Clj mono-cultures at the same time point. Furthermore, cell membrane fusion events were observed in the co-culture, as shown in FIGS. 17C and 17D. Cell fusion was not observed in any of the mono-culture images of Cac and Clj. The cell fusion between Cac and Clj further supports the predicted metabolic coupling in the co-culture. In this particular study, the growth medium contained 60 g/L of glucose and 5 g/L of fructose. As discussed above, Clj is not capable of consuming glucose. As a result, Cac produced a large pool of reducing equivalents during the sugar consumption. In order to survive, Clj had to scavenge for free electrons in order to consume $CO_2$ released during Cac's glucose break down, which was the only carbon source Clj was capable of consuming besides the small amount of fructose in the system. Thus, Clj cells began to fuse with Cac cells in order to acquire the electrons it needed to fuel the $CO_2$ fixation through the WL pathway. Hence, the co-culture cell fusion images show Clj invading the cytoplasm of Cac.

Example 5—$^{13}$C Labeling Experiments to Confirm the Metabolite Exchange Between Cac and Clj To confirm the metabolite exchange between Cac and Clj in co-culture, 50 mM of $^{13}$C-labeled sodium bicarbonate (control: $^{12}$C bicarbonate) was added to the medium to label the $CO_2$. In solution, bicarbonate is protonated to become carbonic acid, which quickly dissociates into $CO_2$ and $H_2O$. Cac controls and co-cultures with a starting Clj/Cac ratio of 20 were used. Each culture was grown under the same conditions. A pure Clj control was not tested, since it would consume $CO_2$ to make acetate and ethanol and, thus, would not provide any useful information. A culture supernatant collected after 30 hours was analyzed using Gas Chromatograph—Mass Spectrometry (GC-MS) to determine the fraction of each product labeled with $^{13}$C.

Figure 18:
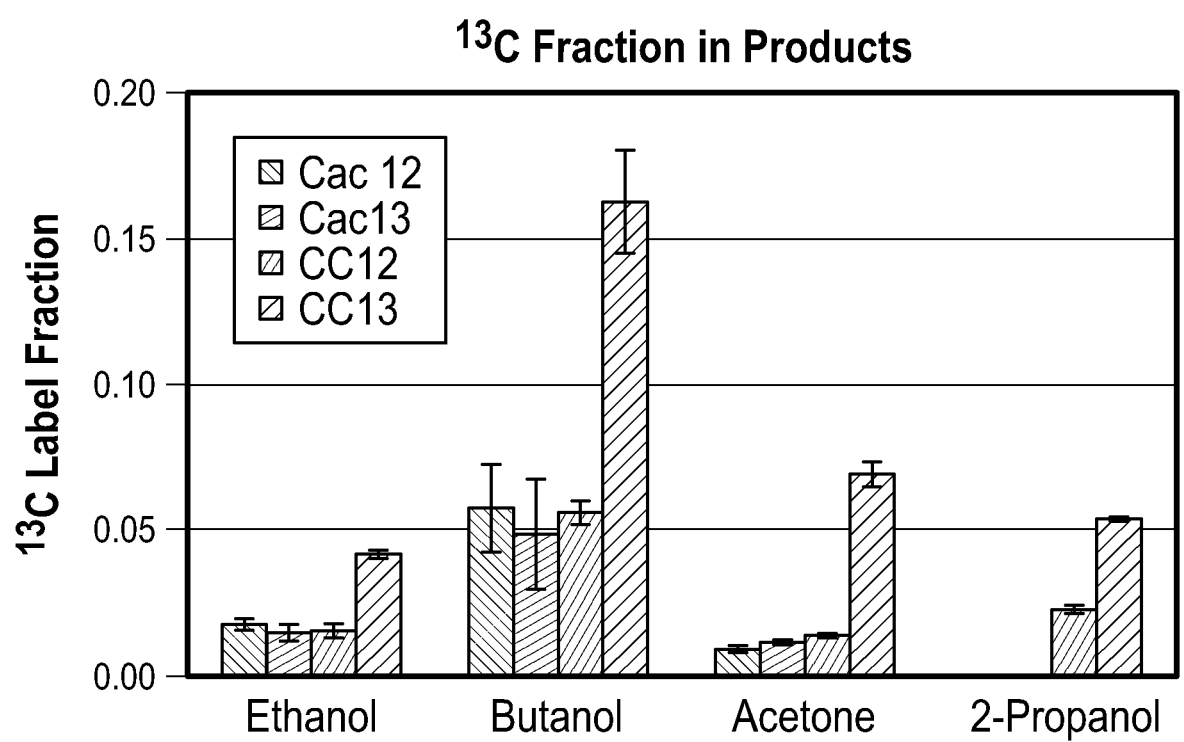
FIG. 18 graphically depicts $^{13}C$ labeling in a co-culture according to the present invention (Example 5).

The data is shown in FIG. 18. As expected, the $^{13}$C fraction in the $^{12}$C Cac control and the $^{12}$C co-culture was low (representing the approximately 1-1.2% natural abundance of $^{13}$C). The fraction was also low in the $^{13}$C Cac control, since Cac cannot fix $CO_2$, although a few exchange reactions may label 4-C metabolites like butanol. The amount of background labeling in each metabolite was also dependent on the number of carbons found in each molecule. As an example, in 2-C ethanol, the background will be approximately 2%, while for 4-C butanol it will increase to approximately 4%.

In comparison, the labeled fraction in the $^{13}$C co-culture increased to 4% for ethanol, 17% for butanol, 7% for acetone, and 6% for isopropanol. Thus, the labeled metabolite fractions were 2- to 4-fold higher in the $^{13}$C co-culture. In the co-culture doped with $^{13}$C bicarbonate, Clj fixes $^{13}CO_2$ to produce $^{13}$C-acetate. The Cac clearly then consumed the labeled acetate to produce labeled ethanol, butanol, and acetone. The labeled fraction of isopropanol was similar to that of acetone, since the conversion by Clj does not involve carbon-carbon bond rearrangements. No labeling data of isopropanol was available for Cac controls, as Cac produces no isopropanol. These results confirmed the hypothesized syntrophic model depicted in FIG. 1.

Example 6—Co-Culture of Strict Anaerobe *C. ljungdahlii* and a Recombinant Strain of Facultative Aerobe *E. coli*

Facultative aerobe *E. coli* has been a laboratory workhorse for decades. As a result, a wide variety of genetic tools have been developed for the genetic manipulation of *E. coli*. This makes *E. coli* an ideal host for expressing almost any metabolic pathway of interest. As such, an *E. coli* strain that expresses three genes from Cac (ctfA, ctfB, and adc), and which are responsible for acetone production, was developed. Similar to Cac, *E. coli* loses approximately 33% of sugar substrate during sugar breakdown to acetyl-CoA. To improve the carbon recovery of *E. coli* fermentation, as well as to increase the diversity of the final products, the acetone-producing *E. coli* strain (hereinafter, "EcoA") was co-cultured together with acetogenic Clj in a manner similar to the Cac-Clj co-culture. The major difference between Cac-Clj co-culture and the EcoA-Clj co-culture is the fact that both Cac and Clj are strictly anaerobic Gram positive bacteria, while EcoA is a Gram negative facultative aerobe. Although both organisms belong to two distinct groups, a successful syntrophic co-culture was still established between EcoA and Clj.

Figure 19:
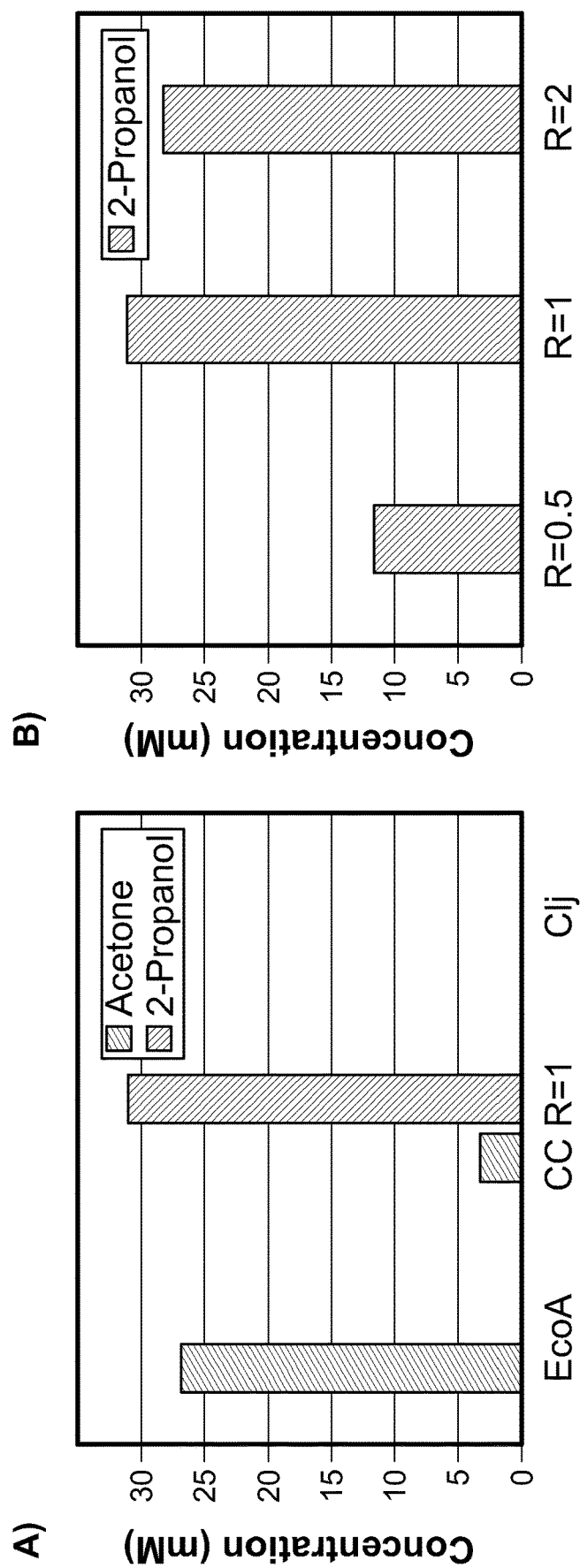
FIG. 19A graphically depicts acetone and 2-propanol production in *E. coli* A (Acetone Strain)—*C. ljungdahii* co-culture compared to pure cultures (Example 6).
FIG. 19B graphically depicts 2-propanol production at various starting *C. ljungdahii/E. coli* A ratios (R-ratios) (Example 6)

As shown in FIG. 19A, the EcoA and Clj controls behaved as expected; EcoA produced 26 mM of acetone, while Clj only produced acetate and ethanol and no higher solvents. In comparison, the EcoA-Clj co-culture produced 4 mM of acetone and 31 mM of 2-propanol. Since neither organism can produce 2-propanol, EcoA and Clj established a syntrophic relationship. EcoA converted the sugar substrate to acetone and Clj utilized excess reducing equivalents produced by the EcoA to reduce acetone to 2-propanol, similar to the Cac-Clj co-culture.

Optimal starting ratios (R-ratios) of Clj/EcoA cells were also examined. As shown in FIG. 19B, the ratios of 0.5, 1, and 2 were tested. The ratio R=1 produced the highest 2-propanol titer of 31 mM. Therefore, the optimal EcoA-Clj co-culture must contain equal amounts of both organisms at the start of the fermentation.

What is claimed is:

1. A syntrophic co-culture comprising:
(a) a first microorganism, wherein the first microorganism is a solventogenic microorganism selected from the group consisting of *Clostridium acetobutylicum, Clostridium beijerinckii, Clostridium butylicum, Clostridium tyrobutyricum, Clostridium pasteurianum, Clostridium saccharobutylicum, Clostridium saccharoperbutylacetonicum, Clostridium akagii, Clostridium algidicarnis, Clostridium arbusti, Clostridium aurantibutylicum, Clostridium Clostridium neopropionicum, Clostridium saccharoacetobutylicum, Clostridium sporogenes, Clostridium tetanomorphum, Clostridium thermoaceticum, Clostridium thermocellum, Clostridium thermobutyricum, Clostridium butyricum,* and *Clostridium cellulovorans,*
(b) a second microorganism, wherein the second microorganism is different from the first microorganism and is selected from the group consisting of acetogenic microorganisms and *Clostridium kluyveri,* wherein the acetogenic microorganisms are selected from the group consisting of *Acetobacterium wieringae, Acetobacterium woodii, Butyribacterium methylotrophicum, Clostridium aceticum, Clostridium autoethanogenum, Clostridium carboxidivorans, Clostridium drakei, Clostridium formicaceticum, Clostridium ljungdahlii, Eubacterium limosum,* and *Moorella thermoacetica,* and wherein the first microorganism and the second microorganism are fused together through their respective cell membranes, and
(c) a growth medium, wherein the growth medium comprises a carbohydrate and exogenous $H_2$, and the carbohydrate is selected from the group consisting of $C_5$ and $C_6$ sugars, oligosaccharides, hemicellulose, cellulose, starches and a combination thereof,
wherein the first microorganism and the second microorganism are present in the co-culture at a ratio in the range of from 1:2.5 to 1:20,
wherein the first microorganism consumes the carbohydrate, and produces $CO_2$, electrons, and at least one other first metabolic product,
wherein the $CO_2$, the electrons, and the at least one other first metabolic product produced by the first microorganism are transferred from the first microorganism into the second microorganism through the cell fusion,
wherein the second microorganism consumes the $CO_2$, the electrons, the at least one other first metabolic product produced by the first microorganism, and the exogenous $H_2$, converts the at least one other first metabolic product by the first microorganism into at least one second product, and produces at least one third metabolic product,
wherein the at least one third metabolic product is transferred from the second microorganism to the first microorganism through the cell fusion, and
wherein the first microorganism consumes the at least one third metabolic product, and produces at least one fourth metabolic product.

2. The co-culture of claim 1, further comprising a third microorganism, wherein the third microorganism is different from the first microorganism and different from the second microorganism.

3. The co-culture of claim 1, wherein the second microorganism is an acetogenic microorganism selected from the group consisting of *Clostridium carboxidivorans, Clostridium autoethanogenum, Clostridium ljungdahlii, Acetobacterium woodii, Moorella thermoacetica,* and *Eubacterium limosum.*

4. The co-culture of claim 1, wherein the second microorganism is *Clostridium kluyveri.*

5. The co-culture of claim 1, wherein the at least one second metabolic product is selected from the group consisting of linear and branched $C_2$ to $C_9$ alcohols, diols, aldehydes, ketones, carboxylic acids, and mixtures thereof.

6. The co-culture of claim 1, wherein the at least one second metabolic product is selected from the group consisting of ethanol, propanols, butanols, pentanols, hexanols, octanols, acetone, butyric acid, acetic acid, caproic acid, butanediols, acetoin, hydroxyl acids, and mixtures thereof.

7. The co-culture of claim 1, wherein the at least one second metabolic product is selected from the group consisting of acetoin, acetone, ethanol, isopropanol, n-butanol, 2,3-butanediol, n-hexanol, n-octanol, and mixtures thereof.

8. The co-culture of claim 1, wherein the first microorganism is *Clostridium acetobutylicum,* and the second microorganism is acetogen *Clostridium ljungdahlii.*

9. The co-culture of claim 1, wherein the at least one other first metabolic product comprises acetate and ethanol.

10. The co-culture of claim 1, wherein the at least one other first metabolic product comprises acetoin and acetone.

11. The co-culture of claim 1, wherein the at least one third metabolic product is selected from the group consisting of acetate, butyrate, hexanoate, octanoate, and ethanol.

12. A method for producing a fermentation product comprising:
(a) providing the co-culture of claim 1; and
(b) fermenting the co-culture to provide at least one fermentation product.

13. The method of claim 12, wherein the at least one fermentation product is selected from the group consisting of linear and branched $C_2$ to $C_9$ alcohols, diols, aldehydes, ketones, carboxylic acids, and mixtures thereof.

14. The co-culture of claim 1, wherein the at least one third metabolic product is selected from the group consisting of isopropanol, 2,3 butanediol, hexanoate, octanoate, butyrate, hexanol, octanol, butanol, and mixtures thereof.

15. The co-culture of claim 1, the first microorganism is *Clostridium acetobutylicum.*

16. The co-culture of claim 1, the first microorganism is *Clostridium acetobutylicum*, and the second microorganism is *Clostridium ljungdahlii* or *Clostridium kluyveri*.

* * * * *